United States Patent
Liu

(10) Patent No.: US 11,667,920 B2
(45) Date of Patent: Jun. 6, 2023

(54) METHODS FOR TREATING BRAIN INJURY

(71) Applicant: The Regents of the University of California, Oakland, CA (US)

(72) Inventor: Da Zhi Liu, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 228 days.

(21) Appl. No.: 16/996,616

(22) Filed: Aug. 18, 2020

(65) Prior Publication Data
US 2021/0095285 A1    Apr. 1, 2021

Related U.S. Application Data

(63) Continuation of application No. PCT/US2019/019235, filed on Feb. 22, 2019.

(60) Provisional application No. 62/634,102, filed on Feb. 22, 2018.

(51) Int. Cl.
*C12N 15/113* (2010.01)
*A61K 31/7105* (2006.01)

(52) U.S. Cl.
CPC ........ *C12N 15/113* (2013.01); *A61K 31/7105* (2013.01); *C12N 2310/141* (2013.01)

(58) Field of Classification Search
None
See application file for complete search history.

(56) References Cited

U.S. PATENT DOCUMENTS

| | | |
|---|---|---|
| 2010/0233084 A1 | 9/2010 | Narasimhaswamy et al. |
| 2013/0028956 A1 | 1/2013 | Fischer et al. |
| 2015/0038506 A1 | 2/2015 | Nacro et al. |
| 2015/0086613 A1 | 3/2015 | Derosa et al. |
| 2015/0152412 A1 | 6/2015 | Avkin-Nachum |
| 2016/0235788 A1 | 8/2016 | Hicks et al. |
| 2017/0065638 A1 | 3/2017 | Fraser |
| 2020/0277676 A1* | 9/2020 | Hicks .................. C12Q 1/6883 |
| 2021/0238593 A1* | 8/2021 | Reddy ................. C12Q 1/6883 |

FOREIGN PATENT DOCUMENTS

WO    2019/165267 A1    8/2019

OTHER PUBLICATIONS

Shen et al. Nitric Oxide 78, 11-21 (Year: 2018).*
Vachev et al., "Characterization of Micro RNA Signature in Peripheral Blood of Schizophrenia Patients using μParaflo™ miRNA Microarray Assay", International Journal of Current Microbiology and Applied Sciences, vol. 5, No. 7, Jul. 10, 2016, pp. 503-512.

* cited by examiner

*Primary Examiner* — Brian Whiteman
(74) *Attorney, Agent, or Firm* — Kilpatrick Townsend & Stockton LLP

(57) ABSTRACT

The disclosure provides methods and pharmaceutical compositions that include a microRNA (miR) or a mimic thereof and a pharmaceutically acceptable carrier for treating brain injuries (e.g., traumatic brain injury (TBI)), preventing or reducing neuronal death, preventing or reducing leukocyte infiltration, and/or preventing or reducing blood-brain barrier (BBB) disruption after brain injuries (e.g., TBI) in a subject. The miR may be selected from the group consisting of miR-125b-5p, miR-122-5p, and a combination thereof. In some embodiments, the methods include administering to the subject the miR or the mimic thereof to decrease the expression level of one or more genes (e.g., Mknk2, Alpk3, and Neu1).

15 Claims, 17 Drawing Sheets
Specification includes a Sequence Listing.

```
                                                    CSs
    3'  aguguucaaucccaGAGUCCCu   5' rno-miR-125b-5p
                  ||||||                        -0.88
779:5' acccgagugccccuuCUCAGGGc...3' Mknk2

3'  aguguucaaucccaGAGUCCCu   5' rno-miR-125b-5p
                  ||||||                        -0.77
454:5' ucuagccuugugacuCUCAGGGu...3' Alpk3

3'  aguguucaaucccaGAGUCCCu   5' rno-miR-125b-5p
                  ||||||                        -0.75
300:5' gugaauagauaugaaCUCAGGGa...3' Neu1
```

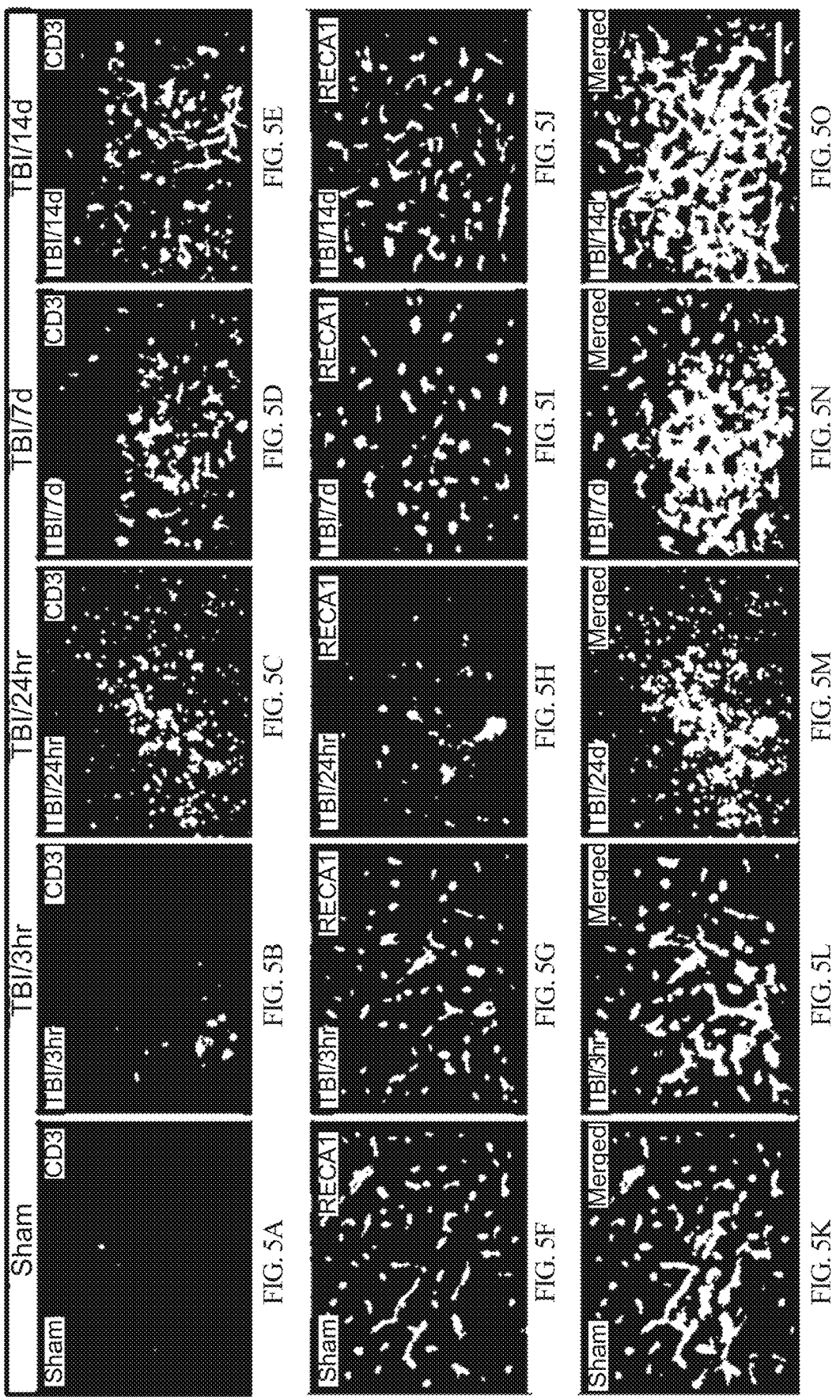

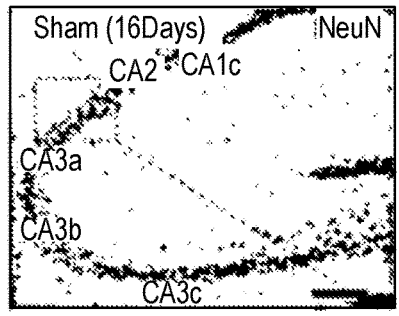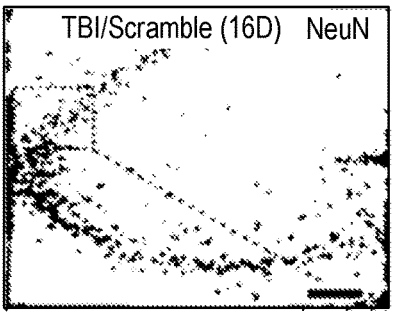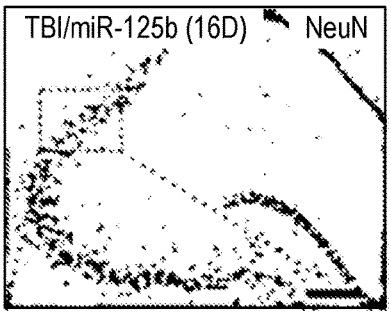
FIG. 8A  FIG. 8C  FIG. 8E
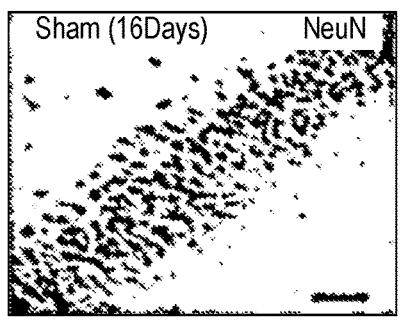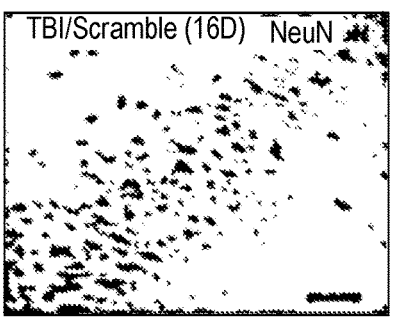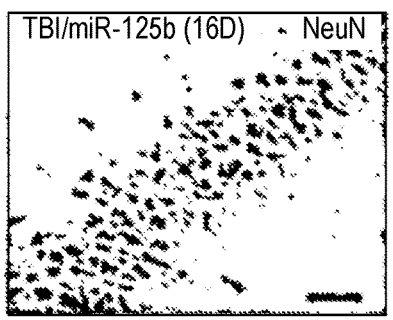
FIG. 8B  FIG. 8D  FIG. 8F
FIG. 9
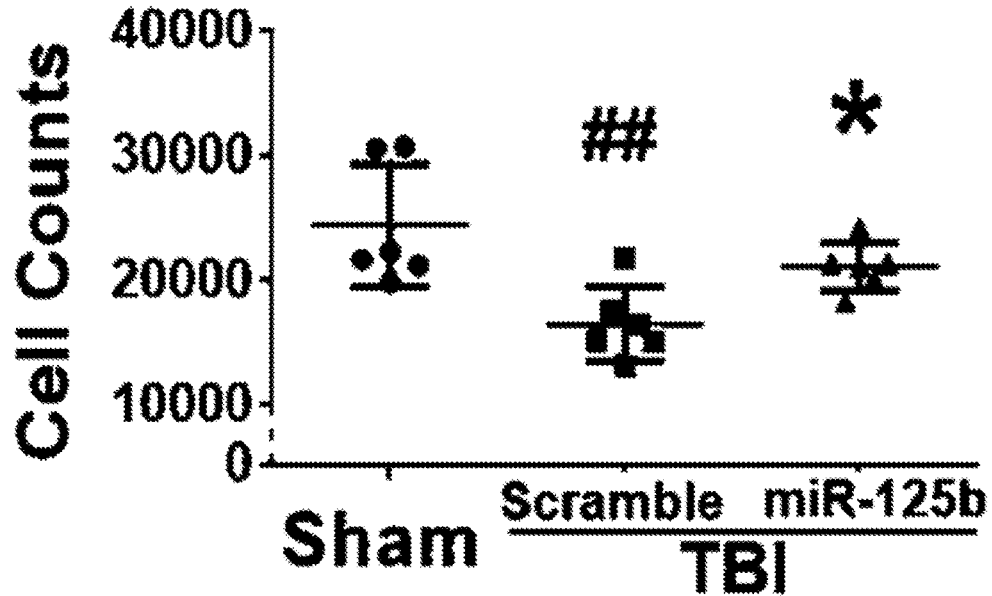

FIG. 12

| Responsive miR-125b targets | Context score (CS) Target Scan | Gene annotation |
|---|---|---|
| Mknk2 | -0.88 | MAP kinase interacting serine/threonine kinase 2 |
| Alpk3 | -0.77 | alpha-kinase 3 |
| Neu1 | -0.75 | sialidase 1 (lysosomal sialidase) |
| Bap1 | -0.57 | BRCA1 associated protein-1 |
| Map3k10 | -0.55 | mitogen-activated protein kinase kinase kinase 10 |
| Tjap1 | -0.21 | tight junction associated protein 1 (peripheral) |
| Mapre2 | -0.39 | microtubule-associated protein, RP/EB family, member 2 |
| Asb13 | -0.35 | ankyrin repeat and SOCS box containing 13 |
| Zdhhc9 | -0.35 | zinc finger, DHHC-type containing 9 |
| Rnf217 | -0.22 | ring finger protein 217 |
| Fam53c | -0.13 | family with sequence similarity 53, member C |
| Zbtb38 | -0.20 | zinc finger and BTB domain containing 38 |
| Ino80d | -0.18 | INO80 complex subunit D |
| Sufu | -0.14 | suppressor of fused homolog (Drosophila) |
| Dusp7 | -0.22 | dual specificity phosphatase 7 |
| Coro2b | -0.12 | coronin, actin binding protein, 2B |
| Wipf2 | -0.27 | WAS/WASL interacting protein family, member 2 |
| Bmpr2 | -0.35 | bone morphogenetic protein receptor, type II |
| Pip4k2b | -0.29 | phosphatidylinositol-5-phosphate 4-kinase, type II, beta |
| Dnajb5 | -0.50 | DnaJ (Hsp40) homolog, subfamily B, member 5 |
| Eif5a2 | -0.31 | eukaryotic translation initiation factor 5A2 |

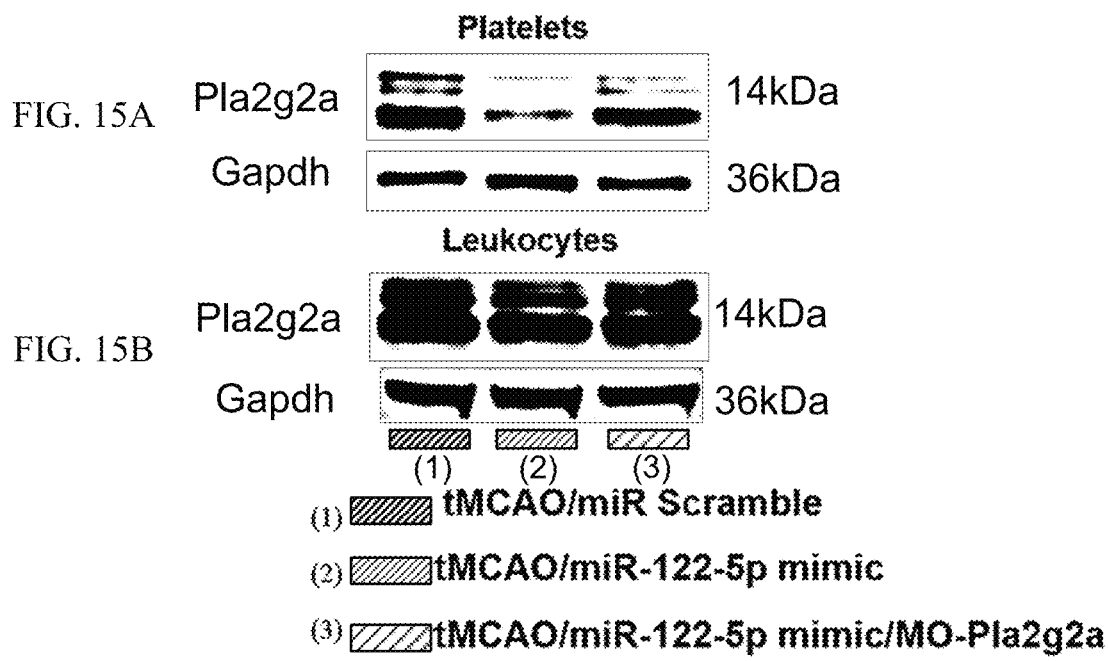
FIG. 15A
FIG. 15B
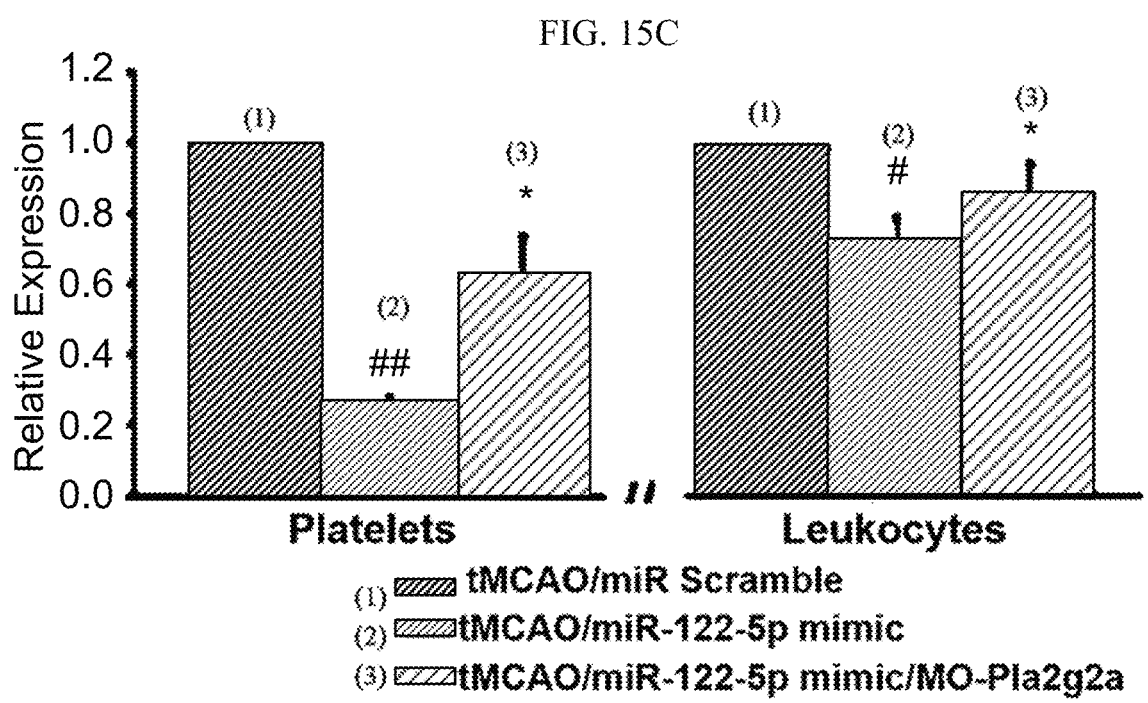
FIG. 15C

SEQUENCE LISTING

```
<160> NUMBER OF SEQ ID NOS: 11

<210> SEQ ID NO 1
<211> LENGTH: 22
<212> TYPE: RNA
<213> ORGANISM: Unknown
<220> FEATURE:
<223> OTHER INFORMATION: Description of Unknown:
      miR-125b-5p sequence

<400> SEQUENCE: 1
ucccugagac ccuaacuugu ga                                            22

<210> SEQ ID NO 2
<211> LENGTH: 22
<212> TYPE: RNA
<213> ORGANISM: Unknown
<220> FEATURE:
<223> OTHER INFORMATION: Description of Unknown:
      miR-122-5p sequence

<400> SEQUENCE: 2
uggaguguga caaugguguu ug                                            22

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
caggctgagc cctgagaag                                                19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtcaggctga gccctgagaa                                               20

<210> SEQ ID NO 5
<211> LENGTH: 23
<212> TYPE: DNA
<213> ORGANISM: Rattus norvegicus

<400> SEQUENCE: 5
tctagccttg tgactctcag ggt                                           23

<210> SEQ ID NO 6
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 6
tgagactcac cctaacttgt ga                                              22

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tgtgactctc agtgttccga tct                                             23

<210> SEQ ID NO 8
<211> LENGTH: 23
<212> TYPE: RNA
<213> ORGANISM: Rattus norvegicus

<400> SEQUENCE: 8
acccgagugc cccuucucag ggc                                             23

<210> SEQ ID NO 9
<211> LENGTH: 23
<212> TYPE: RNA
<213> ORGANISM: Rattus norvegicus

<400> SEQUENCE: 9
ucuagccuug ugacucucag ggu                                             23

<210> SEQ ID NO 10
<211> LENGTH: 23
<212> TYPE: RNA
<213> ORGANISM: Rattus norvegicus

<400> SEQUENCE: 10
gugaauagau augaacucag gga                                             23

<210> SEQ ID NO 11
<211> LENGTH: 22
<212> TYPE: RNA
<213> ORGANISM: Rattus norvegicus

<400> SEQUENCE: 11
ucccugagac ccuaacuugu ga                                              22
```

METHODS FOR TREATING BRAIN INJURY

CROSS-REFERENCE TO RELATED APPLICATIONS

This application is a continuation of International Application No. PCT/US2019/019235, filed Feb. 22, 2019, which claims priority to U.S. Provisional Application No. 62/634,102, filed Feb. 22, 2018, the disclosures of which are hereby incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. R01NS089901, awarded by the National Institutes of Health. The Government has certain rights in this invention.

SEQUENCE LISTING

The present application contains a Sequence Listing which has been submitted electronically in ASCII format and is hereby incorporated by reference in its entirety. Said ASCII copy, created on Jun. 23, 2022, is named SEQ_LIST_070772-225210US-1207930.txt and is 2,385 bytes in size.

BACKGROUND

MicroRNAs (miRs) are regarded as new generation, high-value drug targets[5], and miR therapeutics hold great potential to treat various diseases' since their discovery in the 1990s[42, 43]. The enthusiasm for miR therapeutics is high and is reflected by a large number of pharmaceutical companies pursuing this strategy, mostly for cancer therapy at this time[47]. Drugs that target miRs have been developed rapidly, with several miR drugs advanced to human trials in the last decade, such as anti-miR-122 to treat hepatitis C infection, anti-miR-103/107 to treat diabetes, and anti-miR-155, miR-29 mimic, miR-16 mimic, and miR-34 mimic to treat different types of cancers[5, 44-47]. In addition to most trials which are still in phase I, use of miR-122 to treat hepatitis C infections in patients was successful in phase I and II trials, which has led to additional miR-122 phase II studies with long-term follow-ups, more patients, and multidrug combinations[44]. The progress and success of miR drugs in clinical trials clearly support the feasibility of miR therapy in clinical translation. Although expression profiling of miRs in blood has been studied in both human and experimental traumatic brain injury (TBI)[60, 61], miR drugs have not been tested as therapeutics for TBI.

SUMMARY

In one aspect, the disclosure features a method for treating a brain injury in a subject by administering to the subject a therapeutically effective amount of a microRNA (miR) or a mimic thereof, wherein the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2.

In some embodiments of this aspect, the miR or the mimic thereof decreases the expression level of at least one gene selected from the group consisting of Mknk2, Alpk3, and Neu1.

In some embodiments of this aspect, the expression level is decreased at least 1.5 fold (e.g., 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 fold) relative to the expression level of the gene prior to the administration of the miR or the mimic thereof.

In some embodiments of this aspect, the miR is selected from the group consisting of miR-125b-5p, miR-122-5p, and a combination thereof.

In another aspect, the disclosure features a method for treating a brain injury in a subject by administering to the subject a therapeutically effective amount of a microRNA (miR) or a mimic thereof, wherein the miR is selected from the group consisting of miR-125b-5p, miR-122-5p, and a combination thereof.

In some embodiments of this aspect, the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2. In particular embodiments, the miR or the mimic thereof decreases the expression level of at least one gene selected from the group consisting of Mknk2, Alpk3, and Neu1.

In some embodiments of this aspect, the expression level is decreased at least 1.5 fold (e.g., 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 fold) relative to the expression level of the gene prior to the administration of the miR or the mimic thereof.

In another aspect, the disclosure features a method for preventing or reducing neuronal death after a brain injury in a subject by administering to the subject a therapeutically effective amount of a microRNA (miR) or a mimic thereof, wherein the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2. In some embodiments, the miR or the mimic thereof decreases the expression level of at least one gene selected from the group consisting of Mknk2, Alpk3, and Neu1.

In some embodiments of this aspect, the expression level is decreased at least 1.5 fold (e.g., 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 fold) relative to the expression level of the gene prior to the administration of the miR or the mimic thereof.

In some embodiments of this aspect, the miR is selected from the group consisting of miR-125b-5p, miR-122-5p, and a combination thereof.

In another aspect, the disclosure features a method for preventing or reducing neuronal death after a brain injury in a subject by administering to the subject a therapeutically effective amount of a microRNA (miR) or a mimic thereof, wherein the miR is selected from the group consisting of miR-125b-5p, miR-122-5p, and a combination thereof.

In some embodiments of this aspect, the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2. In particular embodiments, the miR or the mimic thereof decreases the expression level of at least one gene selected from the group consisting of Mknk2, Alpk3, and Neu1.

In some embodiments of this aspect, the expression level is decreased at least 1.5 fold (e.g., 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 fold) relative to the expression level of the gene prior to the administration of the miR or the mimic thereof.

In another aspect, the disclosure features a method for preventing or reducing leukocyte infiltration after a brain injury in a subject by administering to the subject a therapeutically effective amount of a microRNA (miR) or a mimic thereof, wherein the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2. In some embodiments, the miR or the mimic thereof decreases the expression level of at least one gene selected from the group consisting of Mknk2, Alpk3, and Neu1.

In some embodiments of this aspect, the expression level is decreased at least 1.5 fold (e.g., 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 fold) relative to the expression level of the gene prior to the administration of the miR or the mimic thereof.

In some embodiments of this aspect, the miR is selected from the group consisting of miR-125b-5p, miR-122-5p, and a combination thereof.

In another aspect, the disclosure features a method for preventing or reducing leukocyte infiltration after a brain injury in a subject by administering to the subject a therapeutically effective amount of a microRNA (miR) or a mimic thereof, wherein the miR is selected from the group consisting of miR-125b-5p, miR-122-5p, and a combination thereof.

In some embodiments of this aspect, the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2. In some embodiments, the miR or the mimic thereof decreases the expression level of at least one gene selected from the group consisting of Mknk2, Alpk3, and Neu1.

In some embodiments of this aspect, the expression level is decreased at least 1.5 fold (e.g., 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 fold) relative to the expression level of the gene prior to the administration of the miR or the mimic thereof.

In another aspect, the disclosure features a method for preventing or reducing blood-brain barrier (BBB) disruption after a brain injury in a subject, the method comprising administering to the subject a therapeutically effective amount of a microRNA (miR) or a mimic thereof, wherein the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2. In some embodiments, the miR or the mimic thereof decreases the expression level of at least one gene selected from the group consisting of Mknk2, Alpk3, and Neu1.

In some embodiments of this aspect, the expression level is decreased at least 1.5 fold (e.g., 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 fold) relative to the expression level of the gene prior to the administration of the miR or the mimic thereof.

In some embodiments of this aspect, the miR is selected from the group consisting of miR-125b-5p, miR-122-5p, and a combination thereof.

In another aspect, the disclosure features a method for preventing or reducing blood-brain barrier (BBB) disruption after a brain injury in a subject, the method comprising administering to the subject a therapeutically effective amount of a microRNA (miR) or a mimic thereof, wherein the miR is selected from the group consisting of miR-125b-5p, miR-122-5p, and a combination thereof.

In some embodiments of this aspect, the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2. In some embodiments, the miR or the mimic thereof decreases the expression level of at least one gene selected from the group consisting of Mknk2, Alpk3, and Neu1.

In some embodiments of this aspect, the expression level is decreased at least 1.5 fold (e.g., 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 fold) relative to the expression level of the gene prior to the administration of the miR or the mimic thereof.

In some embodiments of the methods described herein, the miR-125b-5p comprises a nucleotide sequence having at least 90% sequence identity (e.g., 92%, 93%, 94%, 95%, 96%, 97%, 98%, 99%, or 100% sequence identity) to UCCCUGAGACCCUAACUUGUGA (SEQ ID NO:1). In some embodiments, the miR-122-5p comprises a nucleotide sequence having at least 90% sequence identity (e.g., 92%, 93%, 94%, 95%, 96%, 97%, 98%, 99%, or 100% sequence identity) to UGGAGUGUGACAAUGGUGUUUG (SEQ ID NO:2).

In some embodiments of the methods described herein, the brain injury is an acute brain injury. In particular embodiments, the acute brain injury is selected from the group consisting of traumatic brain injury (TBI), concussion, intracerebral hemorrhage (ICH), intraventricular hemorrhage (IVH), subarachnoid hemorrhage (SAH), seizure, and ischemic stroke. In some embodiments, the brain injury is caused by a fall, an assault, a motor vehicle accident, a sport or recreational injury, shaken baby syndrome, a gunshot wound, a combat injury, a stroke, an infectious disease (e.g., meningitis or encephalitis), a seizure, an electric shock, a tumor, a toxic exposure, a neurotoxic poisoning (e.g., carbon monoxide poisoning or lead poisoning), a lack of oxygen, or a drug overdose.

In some embodiments of the methods described herein, the miR or the mimic thereof is administered to the subject intravenously, intramuscularly, orally, intradermally, subcutaneously, intraarterially, intraperitoneally, intralesionally, intracranially, intraarticularly, intraprostatically, intrapleurally, intratracheally, intranasally, intravitreally, intravaginally, intrarectally, topically, intratumorally, subconjunctival, intravesicularlly, intrapericardially, intraumbilically, or intraocularally (e.g., intravenously). In some embodiments, the miR or the mimic thereof is administered using a nanoparticle. Particularly, the miR or the mimic thereof may be encapsulated in a nanoparticle (e.g., a liposome (e.g., a polyethylene glycol (PEG) liposome)). In some embodiments of the methods described herein, the subject is a human.

In another aspect, the disclosure features a pharmaceutical composition comprising a microRNA (miR) or a mimic thereof and a pharmaceutically acceptable carrier, wherein the miR is selected from the group consisting of miR-125b-5p (e.g., SEQ ID NO:1), miR-122-5p (e.g., SEQ ID NO:2), and a combination thereof. In some embodiments of the pharmaceutical composition, the miR or the mimic thereof is encapsulated in a nanoparticle (e.g., a liposome (e.g., a polyethylene glycol (PEG) liposome)).

In another aspect, the disclosure features a kit comprising a microRNA (miR) or a mimic thereof and a nanoparticle, wherein the miR is selected from the group consisting of miR-125b-5p (e.g., SEQ ID NO:1), miR-122-5p (e.g., SEQ ID NO:2), and a combination thereof. In some embodiments of the kit, the miR or the mimic thereof and the nanoparticle are provided in separate containers or compartments. In some embodiments, the nanoparticle is a liposome (e.g., a PEG liposome). In some embodiments, the miR or the mimic thereof is encapsulated in the nanoparticle (e.g., the liposome (e.g., a polyethylene glycol (PEG) liposome)).

BRIEF DESCRIPTION OF THE DRAWINGS

FIG. 4A: Expression of miRs alters in blood at 10 min, 30 min, 3 hr, 1 d, 7 d, and 14 d after TBI. FIG. 4B: Expression of miRs alters in blood at 3 hr, 1 d, 7 d, and 14 d after ICH. FIG. 4C: MiRs expression differentially changes in blood at 1 d, 7 d, and 14 d after TBI as compared to ICH.

FIGS. 5A-5O show the time course of T cell ($CD3^+$) infiltration and endothelium ($RECA1^+$) integrity after TBI in rats. Scale bar: 50 µm. n=6/group.

FIGS. 7A-7C: miR-125b-5p mimic prevents bleeding around the injury sites 24 hr after TBI in rats. Scale bar: 150 µm. FIGS. 7D-7L: miR-125b-5p mimic decreased T cell infiltration and increased endothelium integrity 24 hr after TBI in rats. Scale bar: 50 µm. n=6/group.

FIGS. 8A-8F show miR-125b-5p mimic (2.4 mg/kg, i.v. given at 0 hr) promotes CA2/3 neuron survival 16 days post TBI. Each lower panel (FIGS. 8B, 8D, and 8F, scale bars: 50 µm) shows a higher power image of the dash lined area in its upper panel (FIGS. 8A, 8C, and 8E, scale bars: 200 µm).

FIG. 9 shows miR-125b-5p mimic reduces TBI-induced loss of $NeuN^+$ cells in the ipsilateral CA2/3 16 days after TBI. ##P<0.01 vs. sham control;*P<0.05 vs. TBI/scramble. n=6/group.

FIG. 12 shows a list of responsive genes that are decreased 24 hr after miR-125b-5p mimic treatment following TBI and are predicted as miR-125b-5p target genes by TargetScanHuman. Lower CS score indicates high binding affinity of miR-125b-5p to the target gene.

FIGS. 15A-15C show MO-Pla2g2a (12 mg/kg,i.v. given at −15 min prior to MCAO) prevents miR-122-5p mimic-induced reduction of Pla2g2a expression in platelets and leukocytes 24 hr after MCAO. FIG. 15A: Pla2g2a expression in platelets. FIG. 15B: Pla2g2a expression in leukocytes. FIG. 15C: Quantification of Pla2g2a expression in platelets and leukocytes. (1) represents MCAO/scramble miR. (2) represents MCAO/miR-122-5p mimic. (3) represents MCAO/miR-122-5p mimic/MO-Pla2g2a. #P<0.05, ##P<0.01 vs. MCAO/scramble miR; *P<0.05 vs. MCAO/miR-122-5p mimic. n=4/group.

DETAILED DESCRIPTION OF THE EMBODIMENTS

I. Introduction

MicroRNAs (miRs) are considered to be excellent drug targets because: (1) a single miR is capable of modulating numerous target genes by binding to the 3' untranslated region (3'UTR) of these target genes[6-12]; (2) miRs are short (about 22 nucleotides in length) with known sequences from which miR drugs can easily be designed; (3) miRs are often conserved among species including animals and human[69], making miR drugs promising candidates for translation to human diseases and also making it possible to test the therapeutic efficacy of miR in multiple species using the identical miR sequence; (4) miR drugs can be delivered in vivo safely, effectively, and conveniently via several drug delivery systems, such as nanoparticles (e.g., polyethylene glycol 2000 (PEG)-liposomes), which have been approved by the FDA for human use[62]; (5) miR drugs (e.g., miR mimic, miR inhibitors) are already being tested in clinical trials to treat various diseases[5, 44-47].

Blood miRs may be suited for treatment of brain injuries (e.g., TBI) because: (1) alteration of miRs in blood can reflect blood cells (leukocytes, platelets) in response to brain injury, and miRs in blood can be used as biomarkers for certain brain injury (e.g., TBI[70]); (2) miRs are stable in blood[71, 72] which makes them easier to study than mRNA; (3) blood miRs play critical roles in leukocyte infiltration and blood-brain barrier (BBB) disruption, and targeting blood miR can block these pathological processes to treat brain injuries (e.g., TBI[73]); (4) miR drugs targeting blood miRs can be administered intravenously to act on blood cells or endothelium, and thus do not have to be engineered to cross the BBB.

MiR-125b-5p mimic is a chemically modified, double-stranded RNA that is functionally like the native miR-125b-5p, and is incorporated into the RNA-induced silencing complex, which recognizes miR-125b-5p target genes through base-pairing, and decreases their expression by post-transcriptional gene silencing[74, 75]. Therefore, miR-125b-5p mimic can be used to elevate miR-125b-5p that is decreased in blood after a brain injury (e.g., TBI). As described in detail further herein and demonstrated in the examples, blood miR-125b-5p was targeted as the candidate for TBI therapeutics, because (1) miR-125b-5p is one of the two most down-regulated miR in blood following TBI; (2) miR-125b-5p was much more down regulated in TBI than intracerebral hemorrhage (ICH); (3) miR-125b-5p decreases multiple oncogenes/kinases (e.g., Mknk2, Alpk3, Neu1, E2F, JNK, ERK, Akt, and others)[23], in addition to Src which was shown to play a pivotal role in the injury seen with TBI and ICH[19-22].

Figure 1:
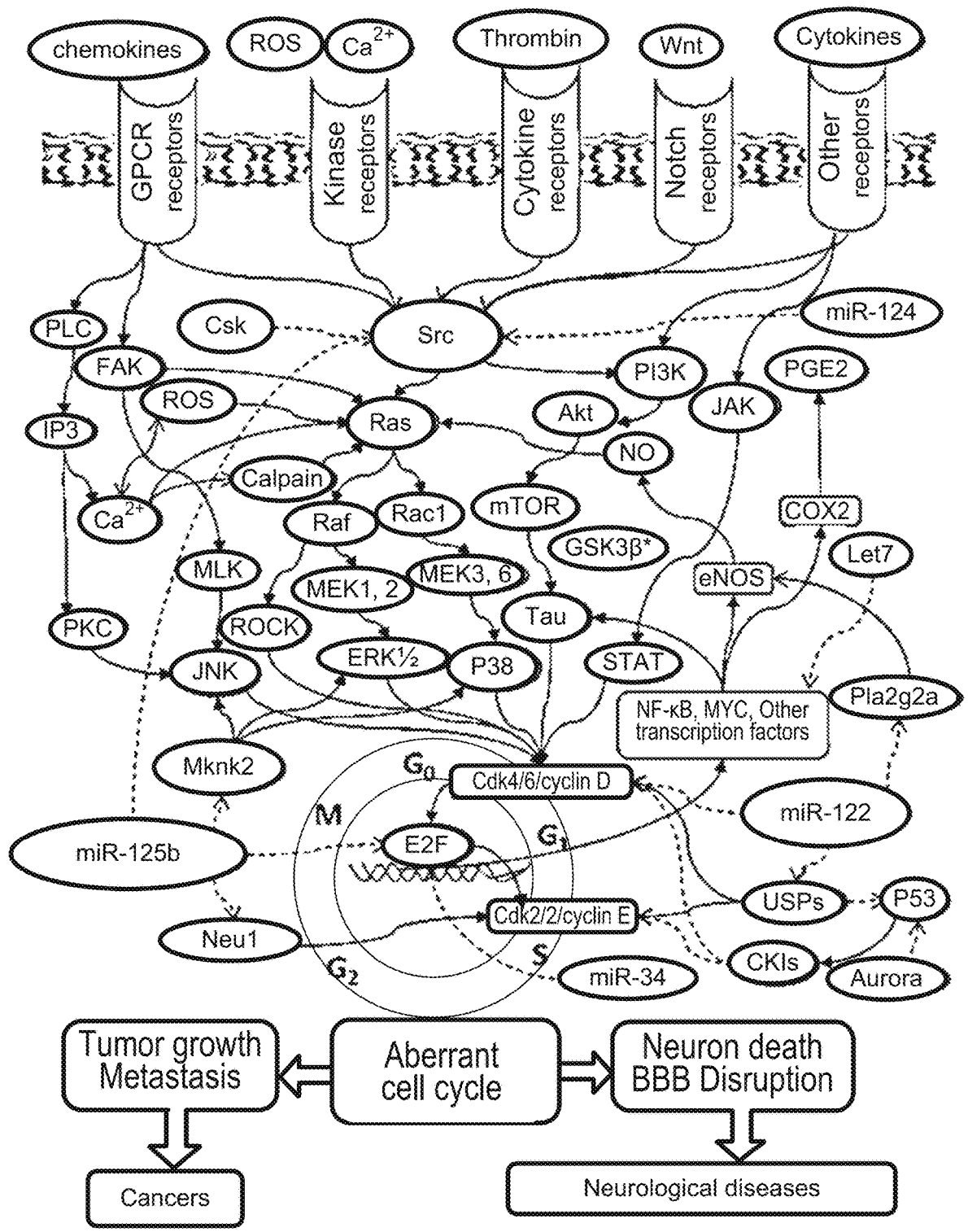
FIG. 1 shows a schematic of oncogenes/kinases and tumor suppressors that are involved not only in tumor growth and metastasis in cancers, but also in neuronal death and blood-brain barrier (BBB) disruption in neurological diseases. The solid lines indicate activation, while the dash lines indicate inhibition. The arrows do not necessarily indicate direct binding to the downstream molecules; intermediate molecules may exist.

Several oncogenes/kinases were the focus of new therapeutic approaches for TBI. The concept of "aberrant cell cycle disease" describes oncogenes/kinases that promote cell division in cancer but also promote mature neuron entry into the cell cycle which results in apoptotic neuronal death[13, 14] (FIG. 1). Moreover, oncogenes/kinases (e.g., Src, Rock, and others) promote cancer cells crossing from blood into tissue to cause metastasis[16, 17]. The same oncogenes/kinases in brain can also mediate leukocyte adhesion to endothelial cells and disrupt of the BBB after TBI[18, 19] (FIG. 1). Indeed, previous studies have demonstrated that systemic administration of oncogene/kinase Src inhibitor (PP2) improves BBB integrity, promotes hippocampal neuron survival, and improves cognitive function after TBI and intracerebral hemorrhage (ICH) in rats[19-22].

Figure 4A:
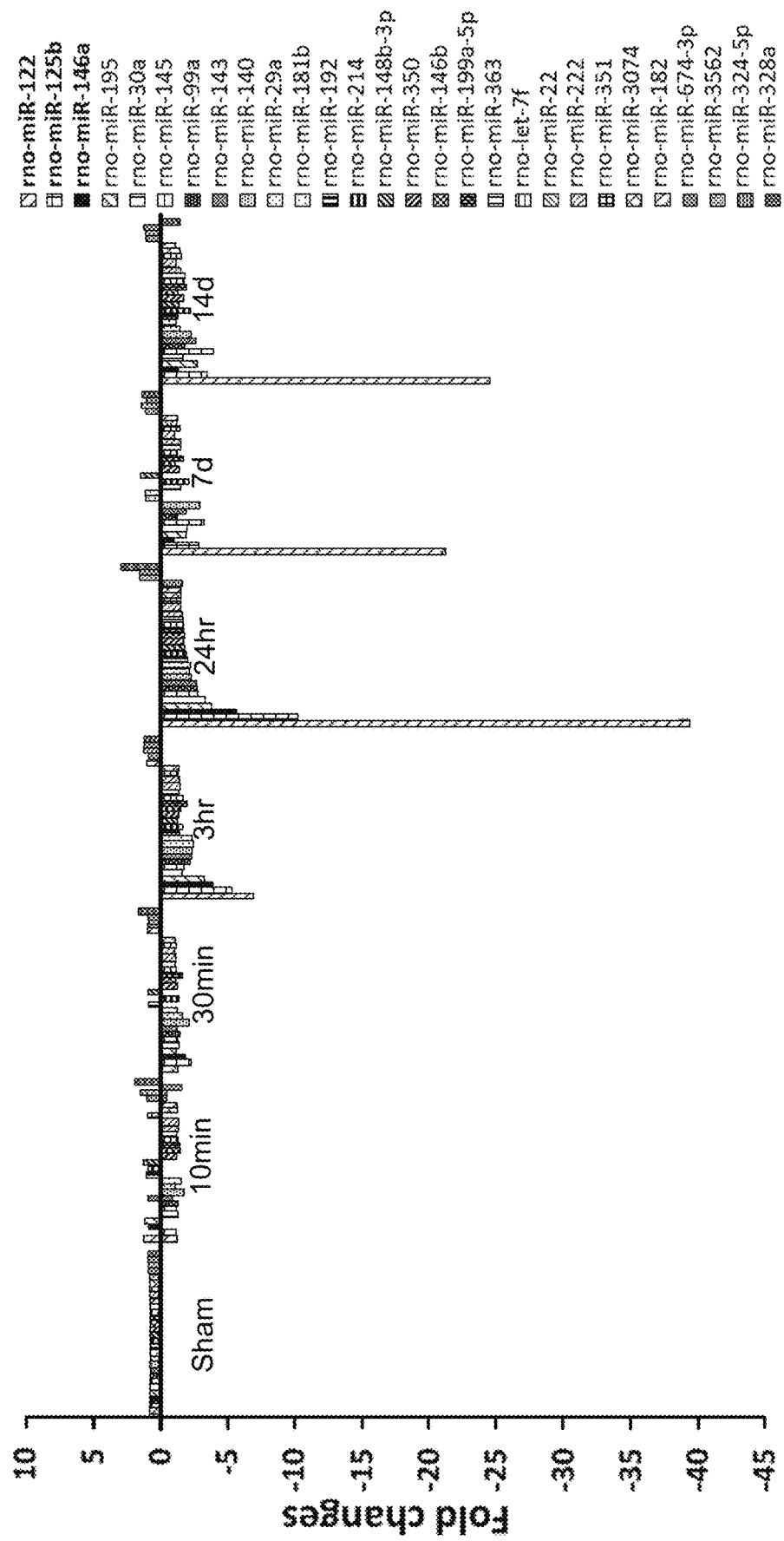
FIGS. 4A-4C show the time course of miRs expression in blood after TBI and ICH in rats.
Figure 4B:
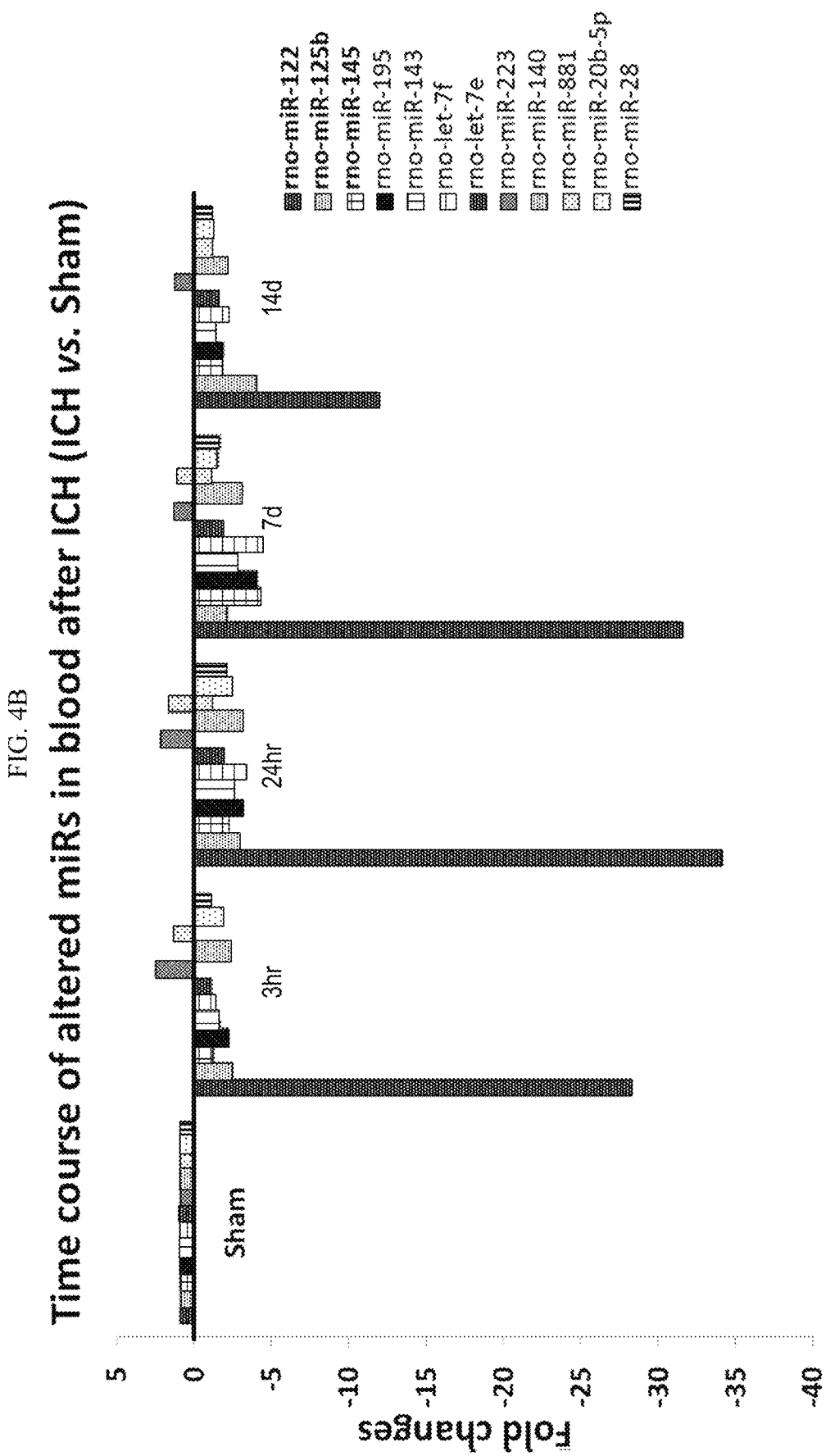
Figure 4C:
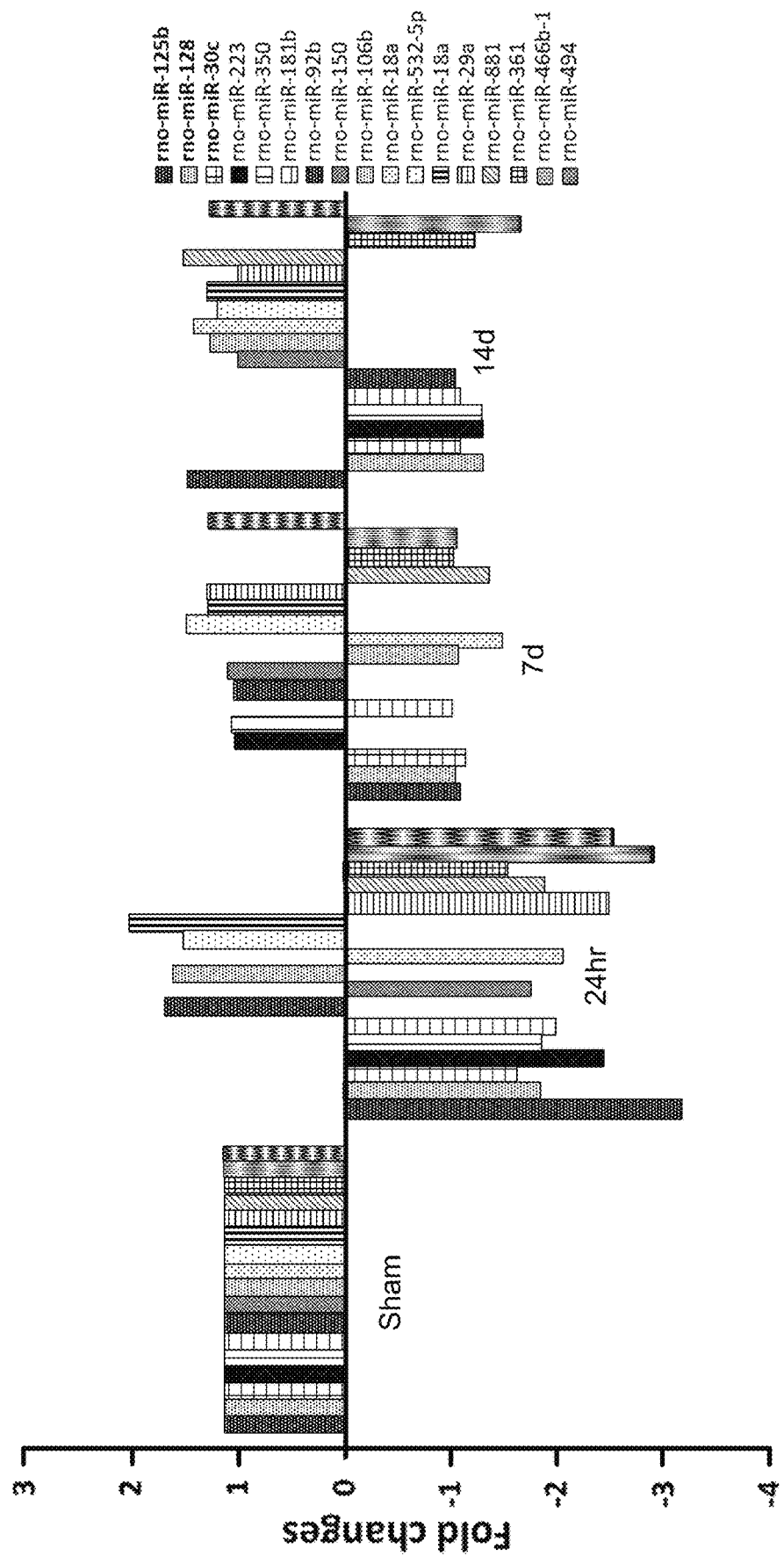
Figure 6:
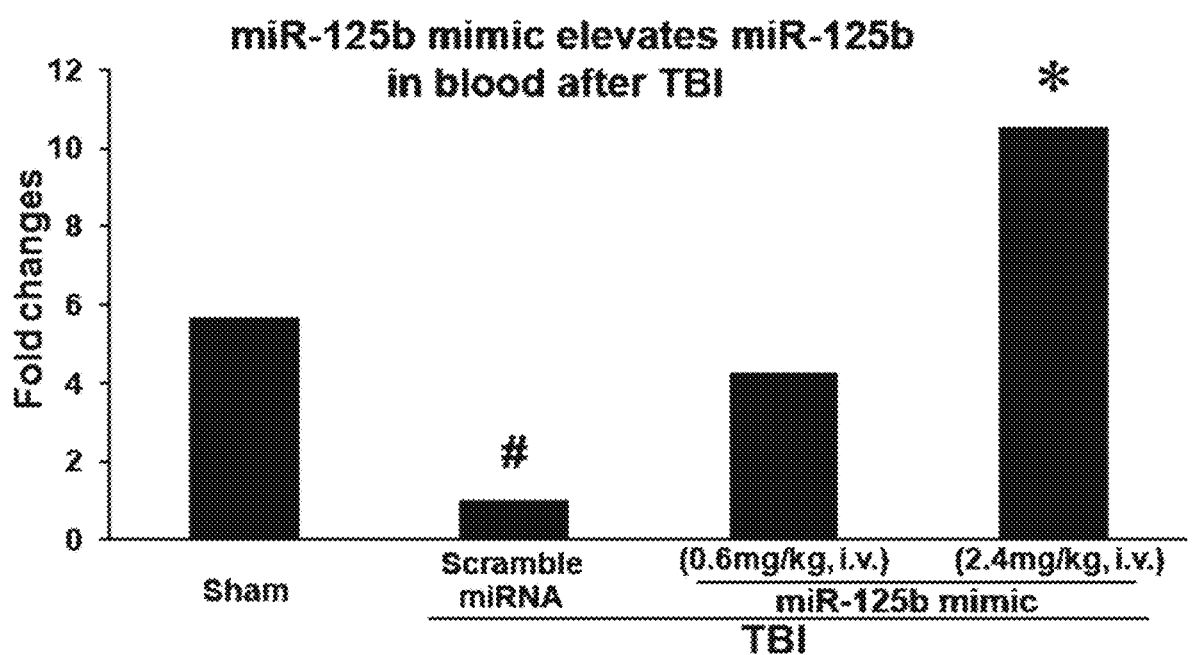
FIG. 6 shows miR-125b-5p mimic (2.4 mg/kg, i.v. given at 0 hr) elevates miR-125b-5p that is decreased in blood 24 hr after TBI. #P<0.05 vs. sham; *P<0.05 vs. TBI/scramble miR. n=6/group.

Elevating miR tumor suppressor in blood may have the potential to treat TBI. A single miR can down-regulate multiple targets by binding to the 3' untranslated region (3'UTR) of its target genes[6-12]. As TBI is often associated with ICH[48-54], blood biomarkers that are altered significantly after TBI and ICH were searched. A rodent lateral fluid percussion (LFP)-induced TBI model, which has been extensively validated and widely used in studies of experimental TBI, and autologous fresh blood-induced non-traumatic ICH model were used to examine the time course of miR expression in blood after TBI and ICH. Young adult male and female rats were used as subjects since TBI is a major problem in young adult humans. Intravenous administration was used as a convenient treatment route. The data showed that several tumor suppressor miRs were decreased in blood after TBI and ICH (FIGS. 4A and 4B). Two miRs (miR-122-5p and miR-125b-5p) were significantly and similarly decreased in blood after both TBI and ICH. Though miR-122-5p decreased more than miR-125b-5p in blood following TBI (FIG. 4A), miR-125b-5p was chosen as a TBI therapy because miR-125b-5p regulates multiple oncogenes/kinases (e.g., Mknk2, Alpk3, Neu1, E2F, JNK, ERK, Akt, and others)[23], in addition to Src which was previously shown plays an important role in affecting histological and behavioral outcomes following TBI and ICH[19-22]. Further, miR-125b-5p was the only one that was differentially altered in TBI as compared to ICH (FIGS. 4A-4C). The decrease of miR-125b-5p reached maximal level in blood 24 hours later, and resolved over time after TBI. This time course of miR-125b-5p expression mirrored that of T cell infiltration after TBI in rats (FIGS. 4 and 5). Preliminary studies on miR-125b-5p found that miR-125b-5p mimic (2.4 mg/kg, i.v., given at 0 hour) increased miR-125b-5p in blood, blocked T cell infiltration, reduced bleeding, prevented endothelium disruption, and decreased hippocampal neuron death post-TBI (FIGS. 6, 7A-7L, and 8A-8F). The results suggest that miR-125b-5p may be used to treat brain injuries such as TBI.

II. Definitions

As used herein, the term "microRNA" or "miR" refers to a small non-coding RNA molecule found in plants, animals, and some viruses, that functions in RNA silencing and post-transcriptional regulation of gene expression. Non-limiting examples are miR-125b-5p (UCCCUGAGACCC-UAACUUGUGA (SEQ ID NO:1)) and miR-122-5p (UG-GAGUGUGACAAUGGUGUUUG (SEQ ID NO:2)).

As used herein, the term "mimic" refers to a synthetic form of a native miR. An miR mimic may comprise the same nucleotide sequence as the native miR or may have at least 90% sequence identity (e.g., 92%, 93%, 94%, 95%, 96%, 97%, 98%, 99%, or 100% sequence identity) to its native miR counterpart. An miR mimic may further include modifications that improve the pharmacokinetics of the mimic, i.e., modification to increase half-life. In general, an miR mimic is functionally the same as its native counterpart and is recognized and incorporated into the RNA-induced silencing complex, which also recognizes target genes that the miR or its mimic binds to through base-pairing. Possible modifications on an miR mimic are described in detail further herein.

As used herein, the term "brain injury" refers to a direct or indirect damage to the brain or head. A brain injury may be caused by a direct or indirect physical damage to the brain or head (i.e., a fall, an assault, or a motor vehicle accident). A brain injury may also be caused by a disease that is directly or indirectly related to the brain or head (i.e., meningitis). A brain injury may be confirmed to one area of the brain or head or involve more than one area of the brain or head. Some symptoms of brain injury include, but are not limited to, neuroinflammation, hypotension, hypoxia, edema, abnormalities in glucose utilization, cellular metabolism, membrane fluidity, synaptic function, and structural integrity of the brain. In some embodiments, a brain injury is an acute brain injury, e.g., traumatic brain injury (TBI), concussion, intracerebral hemorrhage (ICH), intraventricular hemorrhage (IVH), subarachnoid hemorrhage (SAH), seizure, and ischemic stroke.

As used herein, the terms "subject," "individual," and "patient" are used interchangeably herein to refer to a vertebrate, preferably a mammal, more preferably a human. Mammals include, but are not limited to, murines, rats, simians, humans, farm animals, sport animals, and pets. Tissues, cells and their progeny of a biological entity obtained in vivo or cultured in vitro are also encompassed.

As used herein, the term "administering" includes oral administration, topical contact, administration as a suppository, intravenous, intraperitoneal, intramuscular, intralesional, intrathecal, intranasal, intraosseous, or subcutaneous administration to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arterial, intradermal, subcutaneous, intraperitoneal, intraventricular, intraosseous, and intracranial. Other modes of delivery include, but are not limited to, the use of liposomal formulations, intravenous infusion, transdermal patches, etc. In particular embodiments of the methods described herein, the miR or mimic thereof may be administered to the subject intravenously.

As used herein, the term "treating" refers to an approach for obtaining beneficial or desired results including, but not limited to, a therapeutic benefit and/or a prophylactic benefit. By therapeutic benefit is meant any therapeutically relevant improvement in or effect on one or more diseases, conditions, or symptoms under treatment. Therapeutic benefit can also mean to effect a cure of one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. In particular embodiments, beneficial results that may be obtained from the methods for treating a brain injury in a subject described herein include, e.g., prevention or reduction of lymphocyte infiltration (e.g., T cell infiltration), prevention or reduction of blood-brain barrier (BBB) disruption, and prevention or reduction of neuronal death.

As used herein, the term "therapeutically effective amount" refers to an amount, e.g., pharmaceutical dose, effective in inducing a desired biological effect in a subject or patient or in treating a patient having a condition or disorder described herein. It is also to be understood herein that a "therapeutically effective amount" may be interpreted as an amount giving a desired therapeutic effect, either taken in one dose or in any dosage or route, taken alone or in combination with other therapeutic agents. A therapeutically effective amount may be an amount that treats, prevents, alleviates, abates, or reduces the severity of symptoms of diseases and disorders (e.g., a brain injury).

As used herein, the term "pharmaceutical composition" refers to a medicinal or pharmaceutical formulation that contains an active ingredient as well as one or more excipients and diluents to enable the active ingredient suitable for the method of administration. The pharmaceutical composition of the present disclosure includes pharmaceutically acceptable components that are compatible with the miR or mimic thereof. The pharmaceutical composition may be in aqueous form for intravenous or subcutaneous administration or in tablet or capsule form for oral administration.

As used herein, the term "pharmaceutically acceptable carrier" refers to an excipient or diluent in a pharmaceutical composition. The pharmaceutically acceptable carrier must be compatible with the other ingredients of the formulation and not deleterious to the recipient. In the present disclosure, the pharmaceutically acceptable carrier must provide adequate pharmaceutical stability to the miR or mimic thereof. The nature of the carrier differs with the mode of administration. For example, for intravenous administration, an aqueous solution carrier is generally used; for oral administration, a solid carrier is preferred.

As used herein, the term "percent (%) sequence identity" refers to the percentage of amino acid or nucleic acid residues of a candidate sequence that are identical to the amino acid or nucleic acid residues of a reference sequence after aligning the sequences and introducing gaps, if necessary, to achieve the maximum percent identity (i.e., gaps can be introduced in one or both of the candidate and reference sequences for optimal alignment). In some embodiments, percent sequence identity can be any integer from 50% to 100%. In some embodiments, a sequence is substantially identical to a reference sequence if the sequence has at least 50%, 55%, 60%, 65%, 70%, 75%, 80%, 85%, 90%, 91%, 92%, 93%, 94%, 95%, 96%, 97%, 98%, or 99% sequence identity to the reference sequence as determined using the methods described herein; preferably BLAST using standard parameters, as described below.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A comparison window includes reference to a segment of any one of the number of contiguous positions, e.g., a segment of at least 10 residues. In some embodiments, the comparison window has from 10 to 600 residues, e.g., about 10 to about 30 residues, about 10 to about 20 residues, about 50 to about 200 residues, or about 100 to about 150 residues, in which a sequence may be compared to a reference sequence of the same number of contiguous positions after the two sequences are optimally aligned.

Alignment for purposes of determining percent sequence identity can be achieved in various ways that are within the skill in the art, for instance, using publicly available computer software such as BLAST, ALIGN, or Megalign (DNASTAR) software. The BLAST and BLAST 2.0 algorithms are described in Altschul et al. (1990) *J Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. Those skilled in the art can determine appropriate parameters for measuring alignment, including any algorithms needed to achieve maximal alignment over the full length of the sequences being compared. In some embodiments, the percent amino acid or nucleic acid sequence identity of a given candidate sequence to, with, or against a given reference sequence (which can alternatively be phrased as a given candidate sequence that has or includes a certain percent amino acid or nucleic acid sequence identity to, with, or against a given reference sequence) is calculated as follows:

$$100\times(\text{fraction of } A/B)$$

where A is the number of amino acid or nucleic acid residues scored as identical in the alignment of the candidate sequence and the reference sequence, and where B is the total number of amino acid or nucleic acid residues in the reference sequence. In some embodiments where the length of the candidate sequence does not equal to the length of the reference sequence, the percent amino acid or nucleic acid sequence identity of the candidate sequence to the reference sequence would not equal to the percent amino acid or nucleic acid sequence identity of the reference sequence to the candidate sequence.

In particular embodiments, a reference sequence aligned for comparison with a candidate sequence may show that the candidate sequence exhibits from 50% to 100% identity across the full length of the candidate sequence or a selected portion of contiguous amino acid or nucleic acid residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same amino acid or nucleic acid residue as the corresponding position in the reference sequence, then the molecules are identical at that position.

III. MicroRNA Therapeutics and Targets

To understand the mechanisms of how each miR therapeutic works, prediction algorithms that predict potential miR-targets based upon complementary DNA sequences in the miR target genes are available in the art. TargetScan-Human, for example, is a comprehensive web resource for miR-target predictions, and uses an algorithm that incorporates current biological knowledge of miR-target rules including seed-match model, evolutionary conservation, and free binding energy[7, 55]. The target sites predicted by TargetScanHuman are scored for likelihood of mRNA down-regulation using context scores (CS), a regression model that is trained on sequence and contextual features of the predicted miR::mRNA duplex[42, 59]. In large-scale evaluations, TargetScanHuman has been competitive with other target prediction methods in identifying target genes and predicting the extent of their down-regulation at the mRNA or protein levels[42, 59].

To address the question of which targets of miR-125b-5p are responsive to the therapeutic effects of miR-125b-5p after TBI, whole genome microarrays were used first to identify the genes that were decreased in blood after miR-125b-5p mimic treatment after TBI. A miR mimic refers to a synthetic form of a native miR. An miR mimic may comprise the same nucleotide sequence as the native miR or may have at least 90% sequence identity (e.g., 92%, 93%, 94%, 95%, 96%, 97%, 98%, 99%, or 100% sequence identity) to its native miR counterpart. An miR mimic may further include modifications that improve the pharmacokinetics of the mimic, i.e., modification to increase half-life. In general, an miR mimic is functionally the same as its native counterpart and is recognized and incorporated into the RNA-induced silencing complex, which also recognizes target genes that the miR or its mimic binds to through base-pairing. Possible modifications on an miR mimic are described in detail further herein.

Figures 2, 3:
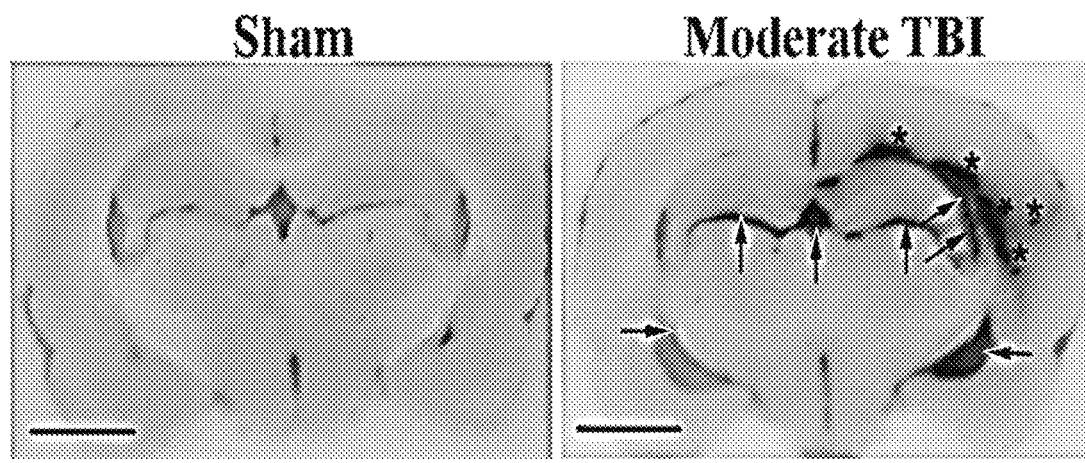
FIG. 2 shows the alignment and CS score of miR-125b-5p to 3'UTR of its target genes: Mknk2, Alpk3, and Neu1. The alignment shows the sites of target gene which miR-125b binds to. Lower CS score (negative number) indicates higher binding affinity of miR-125b to target gene.
FIG. 3 shows images showing hemorrhage distributions in ipsilateral parenchyma and bilateral ventricles at 24 hrs after TBI. Scale bars: 3.25 mm.

Second, a database of all miR-125b-5p targets was built using TargetScanHuman. Third, the genes that were decreased in blood after miR-125b-5p mimic treatment after TBI were compared to the database of miR-125b-5p targets. Fourth, the potential targets were sorted according to the following criteria: (1) decreased in blood after miR-125b-5p mimic treatment after TBI; (2) predicted as miR-125b-5p targets; (3) scored with CS<−0.75; and (4) known as oncogenes/kinases. In terms of these steps and criteria, three miR-125b-5p target genes were identified (FIG. 2).

Once the three best miR-125b-5p target genes (Mknk2, Alpk3, Neu1) as shown in the preliminary data were selected, these genes may be confirmed both in vitro and in vivo by: (1) using luciferase reporter gene assays[56] to validate miR-125b-5p binds to 3'UTR of the targets; and (2) using cell permeable anti-sense in vivo Morpholino Oligos (MO)[57-59] to confirm that miR-125b-5p improves TBI outcome via decreasing mRNA/protein expression of the targets. Based on the alignment of miR-125b-5p to 3'UTR of the three targets (FIG. 2), mutant 3'UTR luciferase plasmids of these targets are created by mutating miR-125b-5p seed-match sequences to confirm the key nucleotides for the binding of miR-125b-5p. Then, based on the alignments shown in FIG. 2, in vivo MOs are designed, synthesized, and used as "antagonists" to specifically compete with miR-125b-5p for binding sites within 3'UTR of each individual miR-125b-5p target gene. For example, the MO designed to compete with miR-125b-5p for 3'UTR of Alpk3 (MO-miR-125b-5p-Alpk3) may block the binding of miR-125b-5p to Alpk3. The disclosure also provides the use of nanoparticles (e.g., PEG-liposomes) to deliver miR-125b-5p into cells following intravenous administration and the use of cell permeable anti-sense in vivo MOs as "antagonists" that compete with miR-125b-5p for binding sites within 3'UTR of each specific miR-125b-5p target gene.

Intravenous miR-125b-5p mimic may decrease oncogenic target genes (e.g., Mknk2, Alpk3, Neu1) in blood to improve the outcome of a brain injury (e.g., TBI). For example, miR-125b-5p mimic may lead to increase of miR-125b-5p, which may lead to decrease of target gene expression, e.g., expressions of Mknk2, Alpk3, and/or Neu1, in leukocytes, platelets, and endothelium. Decrease of Mknk2, Alpk3, and/or Neu1 target gene expression may lead to blockade of lymphocyte infiltration (e.g., T cell infiltration), decrease of BBB disruption, and prevention of neuronal death, which all may improve TBI outcomes.

IV. Methods of the Disclosure

The present disclosure provides methods of treating brain injuries (e.g., TBI) in a subject by administering to the subject a therapeutically effective amount of a microRNA (miR) or a mimic thereof. The disclosure also provides methods for preventing or reducing neuronal death, preventing or reducing lymphocyte infiltration (e.g., T cell infiltration), and/or preventing or reducing blood-brain barrier (BBB) disruption after brain injuries (e.g., TBI) in a subject by administering to the subject a therapeutically effective amount of a miR or a mimic thereof. The methods described herein may prevent brain bleeds, block T cell infiltration, and maintain blood-BBB integrity. Brain injuries may be caused by a number of factors including, but are not limited to, a fall, an assault, a motor vehicle accident, a sport or recreational injury, shaken baby syndrome, a gunshot wound, a combat injury, a stroke, an infectious disease (e.g., meningitis or encephalitis), a seizure, an electric shock, a tumor, a toxic exposure, a neurotoxic poisoning (e.g., carbon monoxide poisoning or lead poisoning), a lack of oxygen, and a drug overdose. In some embodiments of brain injuries, the damage may be direct or indirect to the brain or head. A brain injury may be confirmed to one area of the brain or head or involve more than one area of the brain or head. Some symptoms of brain injury include, but are not limited to, neuroinflammation, hypotension, hypoxia, edema, abnormalities in glucose utilization, cellular metabolism, membrane fluidity, synaptic function, and structural integrity of the brain. In some embodiments, a brain injury is an acute brain injury, e.g., traumatic brain injury (TBI), concussion, intracerebral hemorrhage (ICH), intraventricular hemorrhage (IVH), subarachnoid hemorrhage (SAH), seizure, and ischemic stroke. In particular embodiments, the methods described herein may be used to treat TBI, prevent or reduce neuronal death, prevent or reduce lymphocyte infiltration (e.g., T cell infiltration), and/or prevent or reduce BBB disruption after TBI.

In some embodiments of the methods, the miR or mimic thereof administered to the subject may decrease the expression level of an oncogene/kinase, e.g., at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2. Particularly, the methods described herein may decrease the expression level of at least one gene selected from the group consisting of Mknk2, Alpk3, and Neu1. Methods as described herein for treating brain injuries (e.g., TBI), preventing or reducing neuronal death, preventing or reducing lymphocyte infiltration (e.g., T cell infiltration), and/or preventing or reducing BBB disruption after brain injuries in a subject may include administering to the subject an miR or mimic thereof selected from miR-125b-5p, miR-122-5p, and a combination thereof (e.g., miR-125b-5p). In some embodiments of the methods described herein, the methods may decrease the expression level of the gene (e.g., Mknk2, Alpk3, or Neu1) by at least 1.5 fold (e.g., 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 fold) relative to the expression level of the gene prior to the administration of the miR or the mimic thereof.

Specifically, the methods for treating brain injuries (e.g., TBI), preventing or reducing neuronal death, preventing or reducing lymphocyte infiltration (e.g., T cell infiltration), and/or preventing or reducing BBB disruption after brain injuries in a subject in need thereof may include administering to the subject an miR or mimic thereof selected from miR-125b-5p, miR-122-5p, and a combination thereof (e.g., miR-125b-5p), in which the miR or mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2 (e.g., Mknk2, Alpk3, and Neu1).

miR Mimic

The methods as described herein for treating brain injuries (e.g., TBI), preventing or reducing neuronal death, preventing or reducing lymphocyte infiltration (e.g., T cell infiltration), and/or preventing or reducing BBB disruption after brain injuries in a subject may include administering to the subject an miR-125b-5p or a mimic thereof, an miR-122-5p or a mimic thereof, or a combination thereof. An miR-125b-5p may comprise a nucleotide sequence having at least 90% sequence identity (e.g., 92%, 93%, 94%, 95%, 96%, 97%, 98%, 99%, or 100% sequence identity) to UCCCUGAGACCCUAACUUGUGA (SEQ ID NO:1). An miR-122-5p may comprise a nucleotide sequence having at least 90% sequence identity (e.g., 92%, 93%, 94%, 95%, 96%, 97%, 98%, 99%, or 100% sequence identity) to UGGAGUGUGACAAUGGUGUUUG (SEQ ID NO:2). An miR mimic used in methods described herein may be an miR-125b-5p mimic or an miR-122-5p mimic. In particular embodiments, the miR mimic used in methods described herein is an miR-125b-5p mimic. In some embodiments, an miR mimic may comprise the same nucleotide sequence as the native miR or may contain at least 90% sequence identity (e.g., 92%, 93%, 94%, 95%, 96%, 97%, 98%, 99%, or 100% sequence identity) to its native miR counterpart. An miR mimic may further include modifications that improve the pharmacokinetics of the mimic, i.e., modification to increase half-life. In general, an miR mimic (e.g., miR-125b-5p mimic) is functionally the same as its native counterpart (e.g., miR-125b-5p (SEQ ID NO:1)) and is recognized and incorporated into the RNA-induced silencing complex, which also recognizes target genes that the miR or its mimic binds to through base-pairing. Possible modifications on an miR to create an miR mimic include, but are not limited to, modifications on one or more sugar residues, modifications on one or more internucleoside linkages, and modifications on one or more nucleobases. Modified sugar residues may include, e.g., a pentofuranosyl sugar, a locked sugar, and an unlocked sugar. Modified internucleoside linkages may include, e.g., a phosphorothioate linkage, a phosphorodithioate linkage, and a thiophosphoramidate linkage. Modified nucleobases may include, e.g., hypoxanthine, xanthine, 7-methylguanine, 5,6-dihydrouracil, 5-methylcytosine, and 5-hydroxymethylcytosine.

V. Pharmaceutical Compositions, Preparation, and Delivery

The disclosure features pharmaceutical compositions that include an miR or a mimic thereof and a pharmaceutically acceptable carrier, wherein the miR is selected from the group consisting of miR-125b-5p (e.g., SEQ ID NO:1), miR-122-5p (e.g., SEQ ID NO:2), and a combination thereof. In certain embodiments of the pharmaceutical composition, the miR or the mimic thereof is encapsulated in a nanoparticle (e.g., a liposome (e.g., a polyethylene glycol (PEG) liposome)). In some embodiments, the pharmaceutical composition including an miR (e.g., miR-125b-5p (e.g., SEQ ID NO:1) or miR-122-5p (e.g., SEQ ID NO:2)) or mimic thereof may be formulated for intravenous delivery using a nanoparticle (e.g., a PEG liposome). Further, the disclosure also provides kits containing an miR (e.g., miR-125b-5p (e.g., SEQ ID NO:1) or miR-122-5p (e.g., SEQ ID NO:2)) or a mimic thereof and a nanoparticle (e.g., a PEG liposome). The miR or the mimic thereof and the nanoparticle may be provided in separate containers or compartments. The miR or the mimic thereof may be packaged into the nanoparticle (e.g., a PEG liposome) prior to administration (e.g., intravenous administration).

Nanoparticles used to package and deliver an miR or a mimic thereof as described herein may be lipid-based nanoparticles or polymer-based nanoparticles. Lipid-based nanoparticles are constructed using lipid components and include a vesicle wall containing a single- or double-lipid layer that surrounds a cavity. Examples of lipid-based nanoparticles include, but are not limited to, e.g., liposomes, exosomes, and micelles. Polymer-based nanoparticles are constructed mainly using amphiphilic molecules and amphiphilic polymers, e.g., dodecyltrimethylammonium bromide, sodium dodecylsulfate, betaine, alkyl glycoside, pentaethyllene glycol monododecyl ether, phosphatidylcholine, sodium polyacrylate, poly-N-isopropylacrylamide, poloxamer, and cellulose. Polymer-based nanoparticles may be constructed using one or more types of these amphiphilic molecules and amphiphilic polymers. In addition to the miR or the mimic thereof, the pharmaceutical compositions may contain one or more pharmaceutically acceptable carriers or excipients, which can be formulated by methods known to those skilled in the art. In some embodiments, a pharmaceutical composition of the present disclosure includes an miR-125b-5p (e.g., SEQ ID NO:1) or an miR-122-5p (e.g., SEQ ID NO:2) in a therapeutically effective amount. In certain embodiments, the therapeutically effective amount of the miR or mimic thereof is sufficient to treat the brain injury (e.g., TBI), prevent or reduce neuronal death, prevent or reduce lymphocyte infiltration (e.g., T cell infiltration), and/or prevent or reduce BBB disruption after the brain injury (e.g., TBI). Determination of a therapeutically effective amount is within the capability of those skilled in the art.

Liposome Delivery

In some embodiments, an miR or a mimic thereof may be loaded or packaged in liposomes (e.g., polyethylene glycol 2000 (PEG)-liposomes) for intravenous delivery. The PEG-liposome based drug delivery system has been approved by FDA for human use[62], and has several advantages: (1) it is biodegradable and does not cause toxicity or inflammatory response, (2) the conjugated complexes are stable in serum, and improve the in vivo half-life of the miR or mimic thereof from minutes to hours and enhances the entry of the miR or mimic thereof into cells[76, 77], and (3) it produces a transient elevation of the miR or mimic thereof after administration. It is essential to modulate the miR or mimic thereof transiently to avoid the potential side effects caused by long-term overexpression.

In some embodiments, suitable liposomes may be formed from standard vesicle-forming lipids, which generally include neutral or negatively charged phospholipids and a sterol, such as cholesterol. Embodiments of the disclosure features the package and delivery of the miR or mimic thereof in surface-modified liposomes containing PEG lipids (PEG-modified liposomes). These formulations increase the circulation and accumulation of the miR-containing liposome in target tissues. The long-circulating liposomes are protected from nuclease degradation and enhance the pharmacokinetics and pharmacodynamics of the miR or mimic thereof.

The selection of lipids is generally guided by consideration of factors such as desired liposome size and half-life of liposome in the bloodstream. Further considered are liposomes modified so as to avoid clearance by the mononuclear macrophages and reticuloendothelial systems, for example, having opsonization-inhibition moieties bound to the surface of the liposome structures. Opsonization-inhibition moieties are large hydrophilic polymers bound to the liposome membrane, for example, polyethylene glycol or polypropylene glycol and derivatives thereof, e.g., methoxy derivatives or stearates, or also synthetic polymers such as polyacrylamide or polyvinyl-pyrrolidone, linear, branched, or dendrimeric polyamidoamines, polyacrylic acids, polyalcohols, e.g., polyvinyl alcohols and polyxylitol, and gangliosides. In some embodiments, opsonization-inhibition moieties may be polyethylene glycol or polypropylene glycol and derivatives thereof giving rise to "pegylated liposomes," resulting in stable nucleic acid-lipid particles.

Amphoteric liposomes are another class of liposomes that may be used to delivery the miR or mimic thereof. Amphoteric liposomes are pH dependent charge-transitioning particles that can provide for the delivery of a nucleic acid payload to cells either by local or systemic administration. Amphoteric liposomes can be designed to release their nucleic acid payload within the target cell where the nucleic acid can then engage a number of biological pathways, and thereby exert a therapeutic effect.

Exosome Delivery

In some embodiments, the miR or mimic thereof may be loaded or packaged in exosomes that specifically target a cell type, tissue, or organ to be treated. Exosomes are small membrane-bound vesicles of endocytic origin that are released into the extracellular environment following fusion of mutivesicular bodies with the plasma membrane. Exosome production has been described for many immune cells including B cells, T cells, and dendritic cells. Techniques used to load a therapeutic compound (i.e., an miR or mimic thereof) into exosomes are known in the art and described in, e.g., U.S. Patent Publication Nos. US 20130053426 and US 20140348904, and International Patent Publication No. WO 2015002956, which are incorporated herein by reference. In some embodiments, therapeutic compounds may be loaded into exosomes by electroporation or the use of a transfection reagent (i.e., cationic liposomes).

In some embodiments, an exosome-producing cell can be engineered to produce the exosome and load it with the therapeutic compound. For example, exosomes may be loaded by transforming or transfecting an exosome-producing host cell with a genetic construct that expresses the therapeutic compound, such that the therapeutic compound is taken up into the exosomes as the exosomes are produced by the host cell. In some embodiments, an exosome-targeted protein in the exosome-producing cell may bind (i.e., non-covalently) to the therapeutic compound. Various targeting moieties may be introduced into exosomes, so that the exosomes can be targeted to a selected cell type, tissue, or organ. Targeting moieties may bind to cell-surface receptors or other cell-surface proteins or peptides that are specific to the targeted cell type, tissue, or organ. In some embodiments, exosomes have a targeting moiety expressed on their surface. In some embodiments, the targeting moiety expressed on the surface of exosomes is fused to an exosomal transmembrane protein. Techniques of introducing targeting moieties to exosomes are known in the art and described in, e.g., U.S. Patent Publication Nos. US 20130053426 and US 20140348904, and International Patent Publication No. WO 2015002956, which are incorporated herein by reference.

Preparation

The miR or mimic thereof may be mixed with pharmaceutically acceptable active and/or inert substances for the preparation of pharmaceutical compositions. Compositions and methods for the formulation of pharmaceutical compositions are dependent upon a number of criteria, including, but not limited to, route of administration, extent of disease, or dose to be administered. An miR or mimic thereof used in methods of the disclosure may be utilized in pharmaceutical compositions by combining the miR or mimic thereof with a suitable pharmaceutically acceptable diluent or carrier. A pharmaceutically acceptable diluent includes phosphate-buffered saline (PBS). PBS is a diluent suitable for use in compositions to be delivered parenterally (e.g., intravenously).

In some embodiments, a pharmaceutical composition is prepared for administration by injection (e.g., intravenous, subcutaneous, intramuscular, etc.). In some embodiments, a pharmaceutical composition includes a carrier and is formulated in aqueous solution, such as water or physiologically compatible buffers such as PBS, Hank's solution, Ringer's solution, or physiological saline buffer. Examples of solvents suitable for use in pharmaceutical compositions for injection include, but are not limited to, lipophilic solvents and fatty oils, such as sesame oil, and synthetic fatty acid esters, such as ethyl oleate or triglycerides. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

Acceptable carriers and excipients in the pharmaceutical compositions are nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. In some embodiments, carriers and excipients are selected from water, salt solutions, alcohol, polyethylene glycols, gelatin, lactose, amylase, magnesium stearate, talc, silicic acid, viscous paraffin, hydroxymethylcellulosem, and polyvinylpyrrolidone.

In some embodiments, a pharmaceutical composition of the present disclosure is prepared using known techniques, including, but not limited to mixing, dissolving, granulating, dragee-making, levigating, emulsifying, encapsulating, entrapping, and tabletting processes. In some embodiments, a pharmaceutical composition of the present disclosure is a liquid (e.g., a suspension, elixir and/or solution). In some embodiments, a liquid pharmaceutical composition is prepared using ingredients known in the art, including, but not limited to, water, glycols, oils, alcohols, flavoring agents, preservatives, and coloring agents. In some embodiments, a pharmaceutical composition of the present disclosure is a solid (e.g., a powder, tablet, and/or capsule). In some embodiments, a solid pharmaceutical composition is prepared using ingredients known in the art, including, but not limited to, starches, sugars, diluents, granulating agents, lubricants, binders, and disintegrating agents.

In some embodiments, the miR or mimic thereof may be reconstituted with a suitable diluent, e.g., sterile water for injection. The reconstituted product may be administered as an intravenous infusion after dilution into saline. In some embodiments, the pH of the pharmaceutical composition may be adjusted to pH 7.0-9.0 with acid or base during preparation.

In some embodiments, a pharmaceutical composition is prepared for gene therapy. In some embodiments, the pharmaceutical composition for gene therapy is in an acceptable diluent, or includes a slow release matrix in which the gene delivery vehicle is imbedded. Vectors that may be used as in vivo gene delivery vehicle include, but are not limited to, retroviral vectors, adenoviral vectors, poxviral vectors (e.g., vaccinia viral vectors, such as Modified Vaccinia Ankara), adeno-associated viral vectors, and alphaviral vectors.

VI. Routes, Dosage, and Administration

Pharmaceutical compositions including an miR (e.g., miR-125b-5p (e.g., SEQ ID NO:1) or miR-122-5p (e.g., SEQ ID NO:2)) or a mimic thereof may be formulated for parenteral administration, e.g., intravenous administration, subcutaneous administration, intramuscular administration, intraarterial administration, intrathecal administration, or intraperitoneal administration. In particular embodiments, the pharmaceutical composition may be formulated for intravenous administration. For injectable formulations, various effective pharmaceutical carriers are known in the art, see, e.g., ASHP Handbook on Injectable Drugs, Trissel, 18th ed. (2014). Other administration routes include, but are not limited to, oral, rectal, transmucosal, intestinal, enteral, topical, suppository, through inhalation, intranasal, and intraocular administration.

In some embodiments, administration may include a single dose or multiple doses. In some embodiments, pharmaceutical compositions for injection are presented in unit dosage form, e.g., in ampoules or in multi-dose containers. In particular embodiments, pharmaceutical compositions containing liposomes (e.g., PEG liposomes) packaged with the miR (e.g., miR-125b-5p (e.g., SEQ ID NO:1) or miR-122-5p (e.g., SEQ ID NO:2)) or the mimic thereof may be intravenously administered to the subject in a single dose or multiple doses.

In some embodiments, a pharmaceutical composition described herein is administered in the form of a dosage unit (e.g., bolus). In some embodiments, a pharmaceutical compositions includes an miR (e.g., miR-125b-5p (e.g., SEQ ID NO:1) or miR-122-5p (e.g., SEQ ID NO:2)) or a mimic thereof in a dose selected from 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In some embodiments, a pharmaceutical composition described herein includes a dose of an miR (e.g., miR-125b-5p (e.g., SEQ ID NO:1) or miR-122-5p (e.g., SEQ ID NO:2)) or a mimic thereof selected from 25 mg, 50 mg, 75 mg, 100 mg, 150 mg, 200 mg, 250 mg, 300 mg, 350 mg, 400 mg, 500 mg, 600 mg, 700 mg, and 800 mg. In some embodiments, a pharmaceutical composition includes a dose of the miR (e.g., miR-125b-5p (e.g., SEQ ID NO:1) or miR-122-5p (e.g., SEQ ID NO:2)) or the mimic thereof selected from 50 mg, 100 mg, 150 mg, 200 mg, 250 mg, 300 mg, and 400 mg. In some embodiments, a pharmaceutical composition includes an miR (e.g., miR-125b-5p (e.g., SEQ ID NO:1) or miR-122-5p (e.g., SEQ ID NO:2)) or a mimic thereof in a dose ranging from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg) and, in a more specific embodiment, about 0.1 to about 50 mg/kg and, in a more specific embodiment, about 1 to about 5 mg/kg.

The pharmaceutical compositions are administered in a manner compatible with the dosage formulation and in such amount as is therapeutically effective to result in an improvement or remediation of the symptoms. In some embodiments, the dose is administered at intervals ranging from more than once per day, once per day, once per week, twice per week, three times per week, four times per week, five times per week, six times per week, once per month to once per three months, for as long as needed to sustain the desired effect. The timing between administrations may decrease as the medical condition improves or increase as the health of the patient declines. The dosage may be adapted by the physician in accordance with conventional factors such as the extent of the disease and different parameters of the subject.

EXAMPLES

Example 1—TBI Causes Tissue Contusion and ICH

Experimental LFP-TBI was produced using a fluid percussion device (VCU Biomedical Engineering)[63] in the lateral orientation[64]. Male Sprague-Dawley rats, 300-350 g, were anesthetized, mounted in a stereotaxic, and a 4.8-mm craniotomy performed with a trephine on the right parietal bone. A fluid percussion pulse of 2.15 ATM was delivered to achieve moderate TBI. One day after moderate LFP-TBI, rats were anesthetized and perfused with intracardiac 0.9% saline followed by 4% paraformaldehyde (PFA). Images were taken of rat brains during sectioning. Brain contusion and hemorrhage were observed in ipsilateral parenchyma at 24 hours after TBI (marked with stars) (FIG. 3). Ventricular hemorrhage was also noted (marked with arrows) and the amount of hemorrhage was greater in ipsilateral than contralateral ventricles (FIG. 3). The data show that moderate TBI model produces significant bleeding in brain (Published)[20]. Moreover, this model induced hippocampal neuron loss and memory deficits 16 days after TBI in rats[20]. The following data were obtained using moderate LFP in adult rats, unless stated otherwise.

Example 2—Time Course of miR Expression after TBI and ICH in Rats

Blood was collected in PAXgene tubes via cardiac puncture at different time points (10 min, 30 min, 3 hr, 1 d, 7 d, and 14 d) after TBI or ICH. After total RNA was isolated from blood samples, whole genome miR array was performed to examine miR in each blood sample. The data showed that numerous miRs (e.g., miR-122, miR-125b-5p, miR-146a) were altered more at 1 day, and then decreased at 7 and 14 days post-TBI (FIG. 4A).

Expression of miRs was also examined by whole genome microarrays following Intracerebral Hemorrhage (ICH) (FIG. 4B). Similar to the time course of TBI, several miRs (e.g., miR-122, miR-125b-5p, and miR-145) were altered more at 1 day, and then decreased at 7 and 14 days post-ICH (FIG. 4B).

MiR-125b-5p was selected as the candidate for TBI therapeutics based upon the criteria outlined above, and because it was the second most down regulated miR in blood following TBI or ICH (FIGS. 4A and 4B) and the most down regulated in TBI vs ICH (FIG. 4C). miR-125b-5p decreased 5.3 fold at 3 hrs, 10.2 fold at 24 hrs, 2.8 fold at 7 days, and 3.2 fold at 14 days post-TBI. miR-125b-5p also decreased 2.5 fold at 3 hrs, 2.9 fold at 24 hrs, 2.2 fold at 7 days, and 4.1 fold at 14 days post-ICH (FIGS. 4A and 4B). These preliminary data suggest that miR-125b-5p has the potential to be an early, as well as a late, blood biomarker following TBI.

Example 3—Time Course of T Cell Infiltration into Brain Parenchyma after TBI in Rats To assess T cell infiltration after TBI, brain sections were double labeled with RECA1 (endothelium marker) and CD3 (T cell marker) (FIGS. 5A-5O). There were no CD3$^+$ cells detected either in sham operation animals or 3 hr latter in TBI rats (FIGS. 5A and 5B). CD3$^+$ T cells were observed in brain parenchyma adjacent to TBI injury site 24 hr after TBI (FIG. 5C), and the cells changed morphology at 7 and 14 days after TBI in rats (FIGS. 5D and 5E). Meanwhile, endothelium integrity was remarkably decreased 24 hr after TBI (FIG. 5H), which resolved over time at 7 and 14 days after TBI (FIGS. 5I and 5J).

Example 4—miR-125b-5p Mimic Elevated miR-125b-5p in Blood 24 hr after TBI in Rats MiR-125b-5p mimic or scrambled miR was wrapped in PEG-liposomes, administered i.v. (2.4 mg/kg, given at 0 hr) immediately after TBI, and blood was collected in PAXgene tubes 24 hr later. After total RNA was isolated from blood samples, miR-125b-5p expression was examined in each blood sample. The data showed that miR-125b-5p mimic elevated TBI-induced decrease of miR-125b-5p in blood 24 hr after TBI ($^\#P<0.05$ vs. Sham, $*P<0.05$ vs. TBI/scramble miR, FIG. 6).

Figures 7A, 7B, 7C:
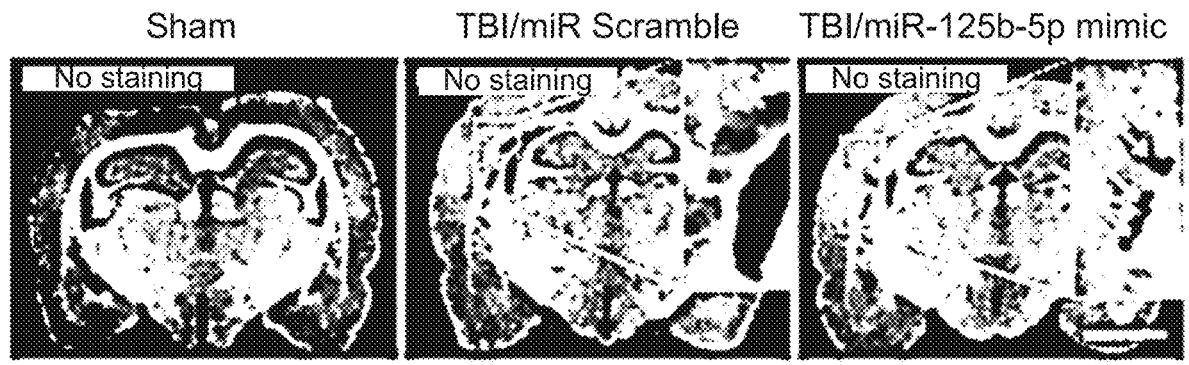
FIGS. 7A-7L show miR-125b-5p mimic (2.4 mg/kg, i.v. given at 0 hr) improved TBI outcomes 24 hr after TBI in rats.
Figures 7D, 7E, 7F:
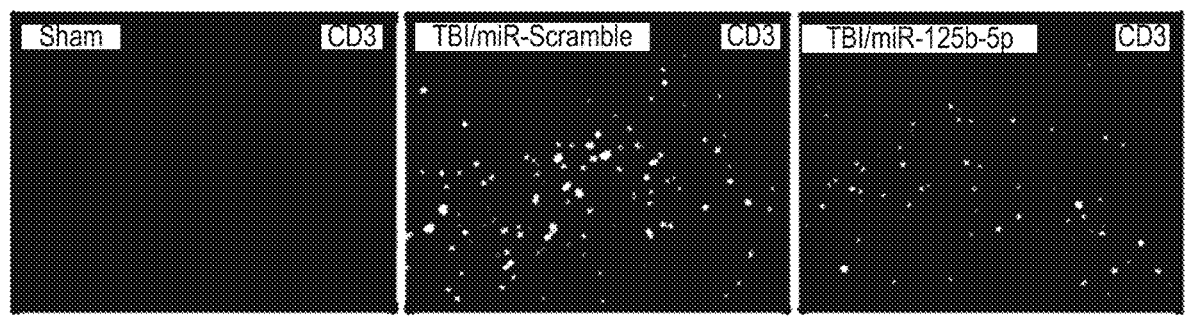
Figures 7G, 7H, 7I:
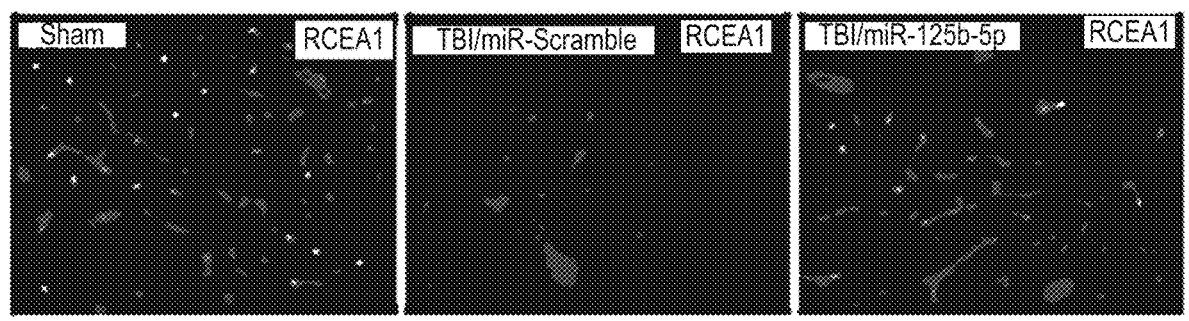
Figures 7J, 7K, 7L:
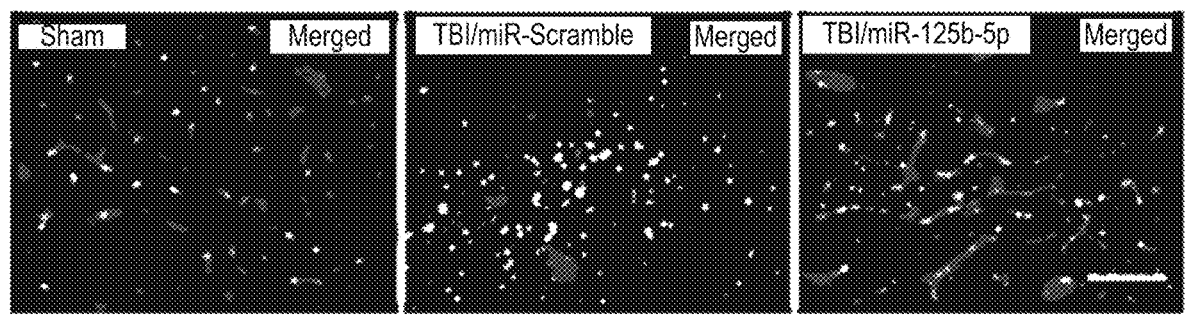

Example 5—miR-125b-5p Mimic Reduced Bleeding, Blocked T Cell Infiltration, and Decreased Endothelial Cell Loss 24 hr after TBI in Rats At 24 hour after TBI, blood clots were noted in rats along the ipsilateral hippocampal alveus adjacent to injury sites in vehicle treated and miR scramble treated (marked with stars within dashed lines in FIG. 7B). miR-125b-5p mimic (2.4 mg/kg, i.v. given immediately after TBI) prevented the blood clots (marked with arrows within dashed lines in FIG. 7C). CD3$^+$ T cells that increased in injury sites following TBI (FIG. 7E) were decreased by miR-125b-5p mimic (2.4 mg/kg, i.v., given at 0 hr) (FIG. 7F). In addition, RECA1 staining of endothelial cells was markedly decreased following TBI (FIG. 7H) compared to sham operated animals (FIG. 7g), and this decreased staining was ameliorated by treatment with miR-125b-5p mimic (2.4 mg/kg, i.v., given at 0 hr) (FIG. 7I). These data show T cell infiltration in areas of BBB injury following TBI, and both can be significantly attenuated by intravenous administration of the miR-125b-5p mimic just after TBI.

Example 6—miR-125b-5p Mimic Prevented Neuronal Loss in Hippocampus Following TBI in Rats After moderate LFP-TBI and treatment with either scrambled miR or miR-125b-5p mimic (2.4 mg/kg, i.v. given at 0 hr), rats at day 16 from each group were anesthetized and perfused with intracardiac 0.9% saline followed by 4% PFA. The coronal frozen sections (50 μm) were cut at −20° C., and the brain sections were immunostained using NeuN. As compared to sham controls (FIGS. 8A and 8B), CA2/3 hippocampal neurons were decreased 16 days (FIGS. 8C and 8D) after TBI. The miR-125b-5p mimic attenuated TBI-induced CA2/3 neuron loss 16 days post-TBI (FIGS. 8E and 8F). Quantification of NeuN$^+$ cell counts at 16 days using unbiased Optical Dissector stereological methods showed that the number of NeuN$^+$ cells decreased in the TBI/scramble group compared to sham surgery control (FIG. 9, $^{\#\#\#}P<0.01$ vs. Sham). Treatment of TBI animals with miR-125b-5p mimic (2.4 mg/kg, i.v.) increased the number of NeuN$^+$ neuronal cells compared to the TBI/ scramble group in the ipsilateral CA2/3 region of hippocampus at 16 days after TBI (FIG. 9, *P<0.05 vs. TBI/scramble miR).

Figure 10:
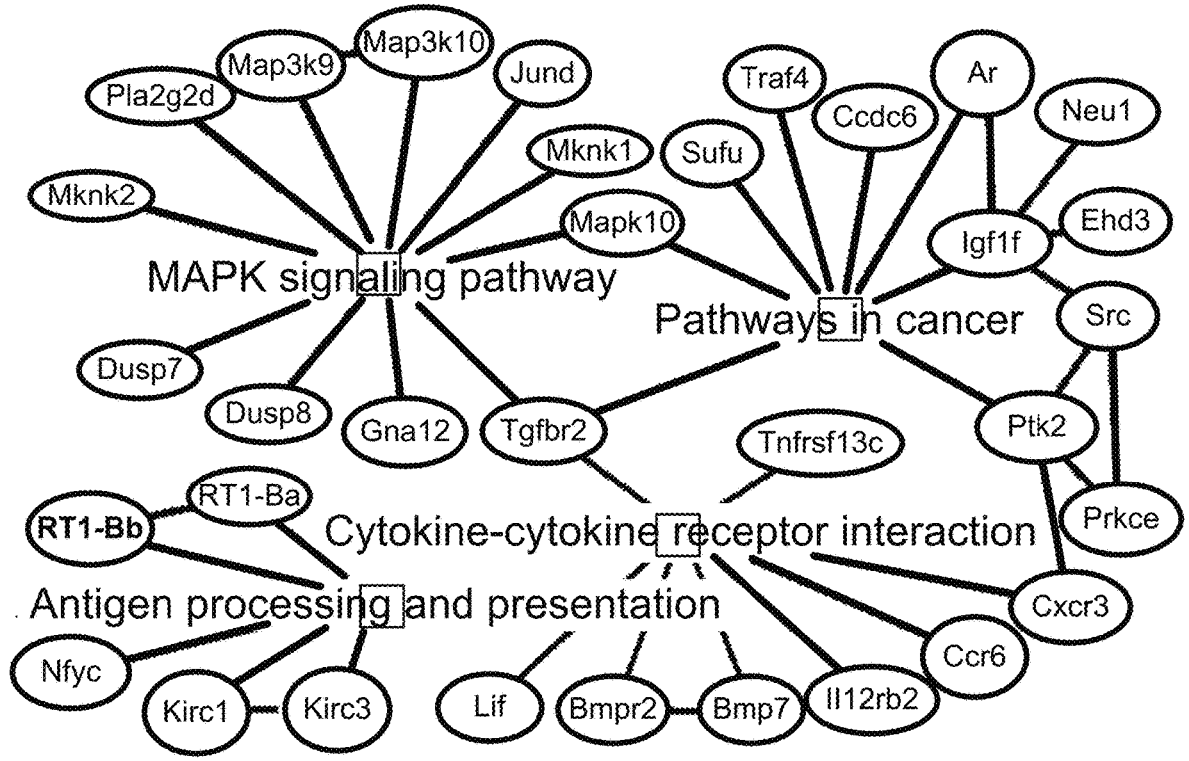
FIG. 10 shows that the top canonical pathways of the oncogenes/kinases and inflammatory genes were decreased in blood 24 hr after miR-125b-5p mimic treatment (2.4 mg/kg, i.v. given at 0 hr) following TBI in rats. n=6/group.

Example 7—miR-125b-5p Mimic Decreased Numerous Genes in Blood 24 hr after TBI in Rats Using whole genome sequencing, it was demonstrated that miR-125b-5p mimic (2.4 mg/kg, i.v. given at 0 hr) significantly down-regulated many genes in blood 24 hr after TBI, including oncogenes/kinases (e.g., Mknk2, Alpk3, Neu1, Src, and others) and inflammatory genes (e.g., Il12rb2, Bmpr2, and others) (P<0.05, Fold change<−1.2) (FIG. 10). The function of the genes that were decreased in blood after miR-125b-5p mimic treatment was predicted using the Kyoto Encyclopedia of Genes and Genomes (KEGG) pathway analyses. The results showed that the top canonical pathways included MAPK signaling pathway, pathways in cancer, cytokine-cytokine receptor interaction, and others (FIG. 10). These data suggest that systemic elevation of miR-125b-5p decreases oncogenic and inflammatory genes in blood which may help explain how it can be used to treat TBI.

Figure 11:
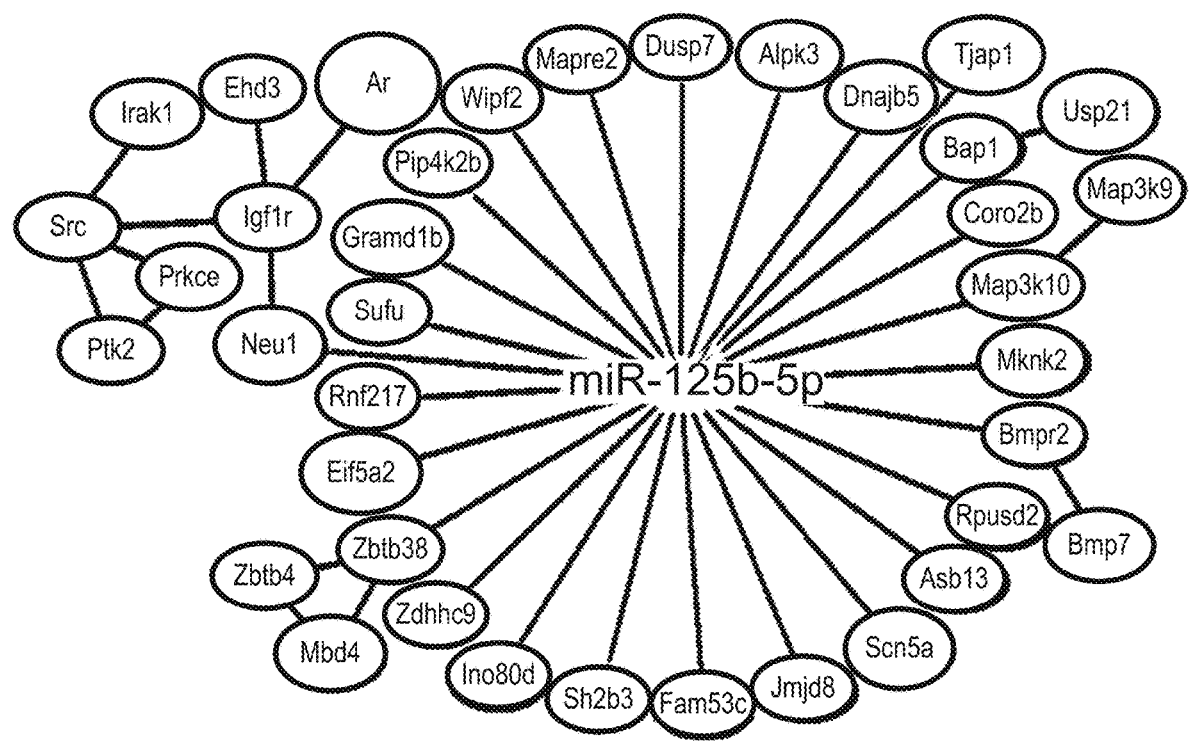
FIG. 11 shows that EGAN analyses show the networking of miR-125b-5p, miR-125b-5p targets (Mknk2, Alpk3, Neu1, others), and their downstream genes (Igf1r, Src and others) that were decreased in blood after miR-125b-5p mimic (2.4 mg/kg, i.v. given at 0 hr) treatment 24 hr following TBI. n=6/group.

Example 8—miR-125b-5p Mimic Decreased its Targets (Mknk2, Alpk3, Neu1) in Blood 24 Hr after TBI in Rats All of the genes that were decreased by miR-125b-5p mimic after TBI were applied to the database of miR-125b-5p targets (TargetScanRat). The data showed that numerous genes (e.g., Mknk2, Alpk3, Neu1) that were decreased in blood by miR-125b-5p mimic treatment (2.4 mg/kg, i.v. given at 0 hr) 24 hr post-TBI, were miR-125b-5p targets predicted by the computational miR-mRNA base-pairing algorithm TargetScanRat (FIG. 12). Using Exploratory Gene Association Networks (EGAN), the networks of miR-125b-5p, miR-125b-5p target genes, and other down-regulated genes (e.g., Igfr1r, Src, Bmp7) are shown (FIG. 11). Note that each target has different CS score (FIG. 12), and lower CSs indicates higher likelihood for miR-125b-5p binding to the predicted target. Using a stringent cut-off (CSs<−0.75), the number was narrowed to three miR-125b-5p targets (e.g., Mknk2, Alpk3, Neu1) that are more likely to mediate the therapeutic effects of miR-125b-5p on TBI (FIG. 12).

Example 9—miR-125b-5p Mimic and miR-122-5p Mimic Improve Cognitive Outcome after TBI in Rats Morris Water Maze Spatial memory was assessed using the Morris water maze on days 11 through 15 after TBI. The apparatus and methods are described previously[20,87]. In brief, rats received a total of 4 trials per day, one from each different starting point, over 5 consecutive days. A probe trial without the platform was performed 24 hours after the last trial. Mean latency to find the platform was calculated for each day to assess learning only when the mean swimming speed (motor function) was not different between groups. Behavioral assessments were performed by an investigator blinded to the treatment groups. Statistical differences were determined using repeated measures ANOVA followed by Dunnett's post hoc test.

Figure 17:
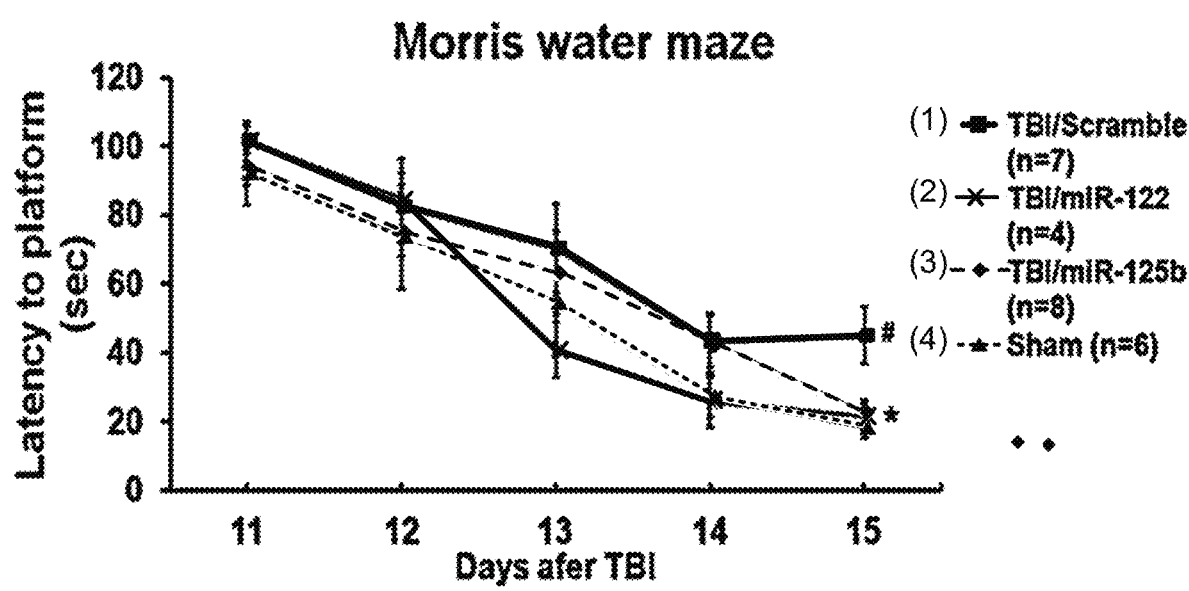
FIG. 17 shows that miR-125b-5p mimic and miR-122-5p mimic reduced cognitive decline 11-15 days after TBI in rats. #P<0.05 TBI/miR-scramble vs. sham; *P<0.05 TBI/miR-125b-5p vs. TBI/miR-scramble.

Morris water maze was conducted to examine cognitive function at 11 through 15 days after TBI. Line (1): TBI/miR-scramble (2.4 mg/kg, i.v); line (2): TBI/miR-122-5p mimic (2.4 mg/kg, i.v.); line (3): TBI/miR-125b-5p mimic (2.4 mg/kg, i.v.); and line (4): sham operation (sham). The TBI/miR-scramble group had significantly longer latencies to find the hidden platform compared to sham (#P<0.05, FIG. 17). Treatments with miR-125b-5p mimic (2.4 mg/kg, i.v.) significantly improved Morris water maze performance compared to the TBI/miR-scramble (*P<0.05, FIG. 17). miR-122-5p mimic (2.4 mg/kg, i.v.) decreased the latency compared to the TBI/miR-scramble (FIG. 17).

Example 10—Competitive Binding of Morpholino Oligos (MO)

This experiment demonstrated competitive binding of Morpholino Oligos (MO) with miR-125b-5p for 3'UTR binding site in target genes in vitro and in vivo. The key methods to study miR-target interaction include: constructs of wild-type and mutant 3'UTR luciferase plasmid, and constructs of Morpholino Oligos (MO) that can compete with miR drug for binding sites in 3'UTR of miR targets in vitro and in vivo. These methods were established in a separate project using miR-122-5p mimic to treat ischemic stroke (MCAO) in rats.

Figure 13:
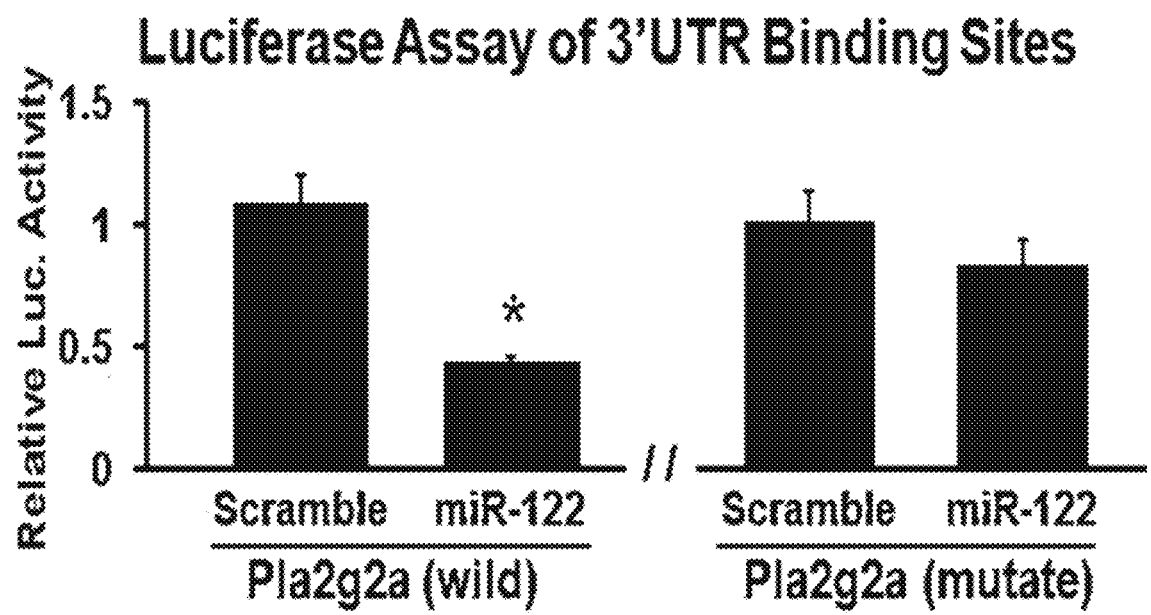
FIG. 13 shows miR-122-5p (50 nM) decreases luciferase activity of 3'UTR of Pla2g2a (wild) (Left Panel), but not of the mutated 3'UTR of Pla2g2a (Right Panel). *p<0.05 vs. Scramble miR. n=3/group.
Figure 14:
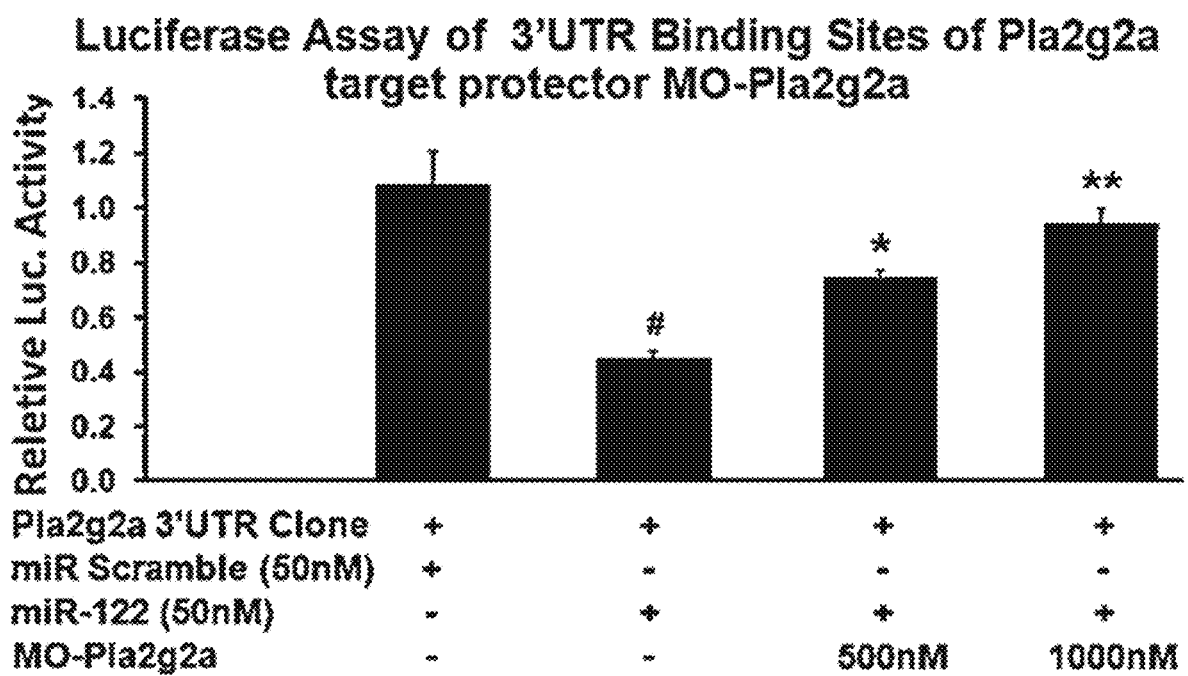
FIG. 14 shows MO-Pla2g2a (500, 1000 nM) prevents miR-122-5p (50 nM)-induced decrease of luciferase activity of Pla2g2a 3'UTR clone. #p<0.05 vs. Pla2g2a 3'UTR/Scramble miR; *p<0.05, **P<0.01 vs. Pla2g2a 3'UTR/miR-122-5p. n=3/group.

Briefly, 3'UTR or mutated 3'UTR (mutated miR-122-5p seed-match sequences) of Pla2g2a luciferase plasmids were constructed and cloned to a luciferase reporter, co-transfected with miR-122-5p enhancer or scrambled miR, and assayed luciferase activity 48 hr after transfection. The data showed that miR-122-5p (50 nM) significantly produced a 50% reduction in luciferase activity when luciferase vector was inserted with Pla2g2a 3'UTR 48 hr after co-transfection (*P<0.05 vs. Pla2g2a 3'UTR/Scramble miR, Left panel, FIG. 13), but miR-122-5p (50 nM) had little effects on luciferase activity when mutated Pla2g2a 3'UTR was present (Right panel, FIG. 13). Using the miR-122-5p seed-match sequences within 3'UTR of Pla2g2a, MO-Pla2g2a was constructed. MO-Pla2g2a was co-transfected with miR-122-5p and luciferase reporter cloned with wild-type Pla2g2a 3'UTR. Luciferase activity was detected 48 hr later. The data showed in vitro MO-Pla2g2a (500, 1000 nM) prevented miR-122-5p (50 nM)-induced decrease of luciferase activity of Pla2g2a 3'UTR clone 48 hr after transfection (#P<0.05 vs. Pla2g2a 3'UTR/Scramble miR; *P<0.05, **P<0.01 vs. Pla2g2a 3'UTR/miR-122-5p, FIG. 14). In addition, in vivo MO-Pla2g2a (12 mg/kg, i.v. given at −15 min) blocked miR-122-5p mimic (2.4 mg/kg, i.v. given at 0 hr)-induced reduction of Pla2g2a expression in platelets and leukocytes 22.5 hr after 1.5 hr MCAO in rats (#P<0.05, ##P<0.01 vs. MCAO/scramble miR; *P<0.05 vs. MCAO/miR-122-5p mimic) (FIGS. 15A-15C).

Figure 18:
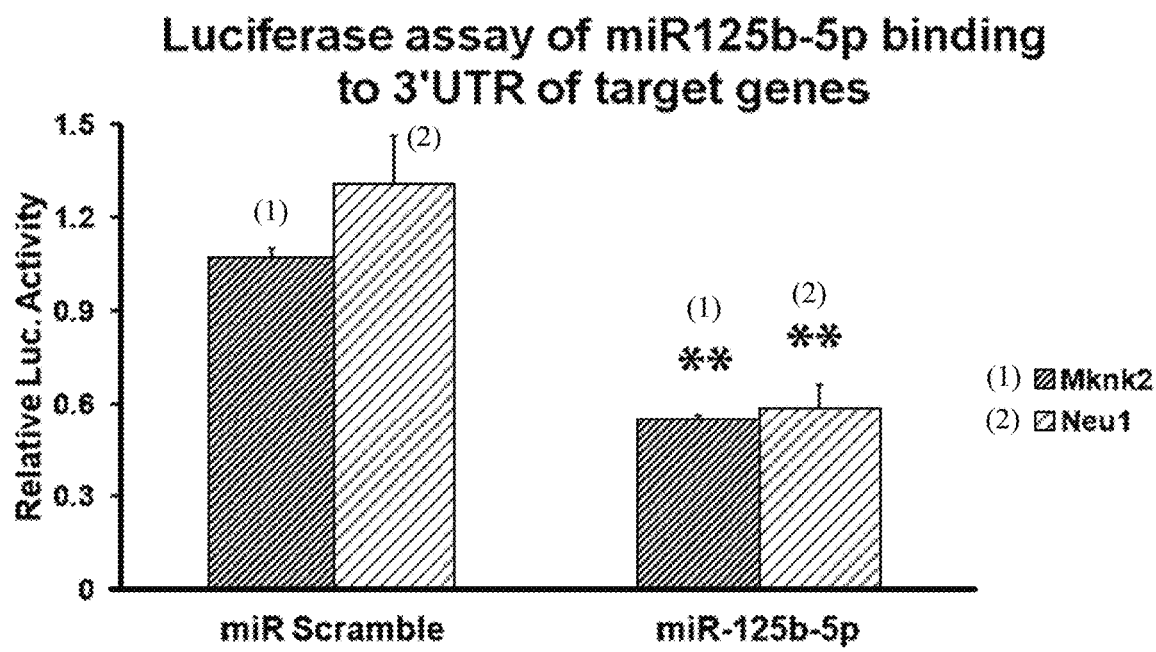
FIG. 18 shows miR-125b-5p (50 nM) decreased luciferase activity of 3'UTR clones of Mknk2 and Neu1, respectively (**P<0.01 vs. 3'UTR clone/miR-scramble). n=3/group.
Figure 19:
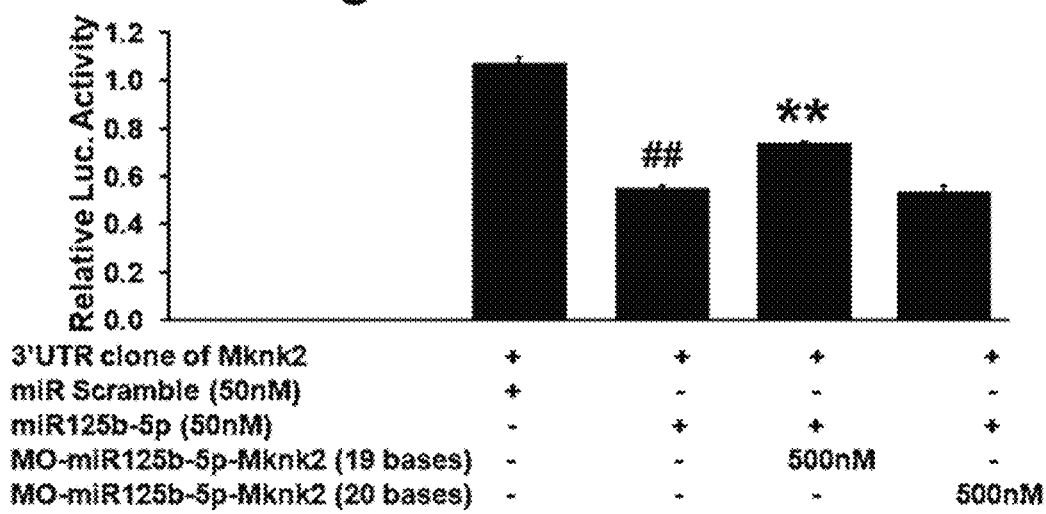
FIG. 19 shows in vitro MO-miR-125b-5p-Mknk2 (19 bases, CAGGCTGAGCCCTGAGAAG (SEQ ID NO:3)) (500 nM) prevented miR125b-5p-induced decrease of luciferase activity of Mknk2 3'UTR clone, whereas MO-miR-125b-5p-Mknk2 (20 bases, GTCAGGCTGAGCCCTGAGAA (SEQ ID NO:4)) (500 nM) had little effects. (##P<0.01 vs. Mknk2 3'UTR/miR-scramble; **P<0.01 vs. Mknk2 3'UTR/miR-125b-5p). n=3/group.

As for miR-125b-5p target binding experiments, 3'UTR of Mknk2 and Neu1 luciferase plasmids were constructed and cloned to a luciferase reporter, co-transfected with miR-125b-5p enhancer or scrambled miR, and assayed luciferase activity 48 hr after transfection. The data showed miR-125b-5p (50 nM) significantly produced ~50% reduction decreased luciferase activity of 3'UTR clones of Mknk2 and Neu1, respectively (P<0.01 vs. 3'UTR clone/miR-scramble) (FIG. 18). Using the miR-125b-5p seed-match sequences within 3'UTR of Mknk2, MO-miR-125b-5p-Mknk2 was constructed. MO-miR-125b-5p-Mknk2 was co-transfected with miR-125b-5p and luciferase reporter cloned with wild-type Mknk2 3'UTR. Luciferase activity was detected 48 hr later. The data showed in vitro MO-125b-5p-Mknk2 (19 bases, CAGGCTGAGCCCT-GAGAAG (SEQ ID NO:3)) (500 nM) prevented miR125b-5p-induced decrease of luciferase activity of Mknk2 3'UTR clone, whereas MO-miR-125b-5p-Mknk2 (20 bases, GTCAGGCTGAGCCCTGAGAA (SEQ ID NO:4)) (500 nM) had little effects (##P<0.01 vs. Mknk2 3'UTR/miR-scramble; P<0.01 vs. Mknk2 3'UTR/miR-125b-5p) (FIG. 19). These results confirmed that MO-miR-125b-5p-Mknk2 competes with miR-125b-5p for the binding sites within 3'UTRs of Mknk2.

Example 11—Dose Dependency of miR-125b-5p Mimic

The goal of this experiment is to demonstrate that miR-125b-5p mimic (1.2, 2.4, 4.8 mg/kg, i.v. given at 0 hr) dose-dependently improves outcomes 24 hr after TBI in rats, including decreasing of bleeding, decreasing of T cell infiltration, and preventing of BBB disruption.

Animal Groups and miR-125b-5p Mimic Treatments in TBI Rats

LFP-induced TBI surgery is performed as described below. Rats are grouped due to different doses of miR-125b-5p mimic (1.2, 2.4, 4.8 mg/kg) after TBI. Briefly, rats (n=80) are divided into 5 groups (each group of 16 rats including 2 sub-groups: 8 male, 8 female). The 5 groups include: TBI sham operation (Group 1); TBI/miR scramble (Group 2); TBI/miR-125b-5p mimic of 1.2, 2.4, and 4.8 mg/kg (Groups 3-5). The miR-125b-5p mimic is administered within 15 minutes after TBI to produce maximal improvement in outcomes. Animals are euthanized at 24 hr and brains assessed for TBI-induced hemorrhage, T cell infiltration, and BBB disruption.

Animals, Pre- and Post-Surgical Procedures, and Blind Outcome Assessments

Sprague-Dawley rats of both sexes, weighing 275-300, are purchased from Envigo. After a 14-day acclimation period to the new environment, the rats are used for surgeries for moderate lateral fluid percussion (LFP)-induced TBI. Animals are monitored for body temperature, blood pressure, pulse, and blood gases throughout and excluded if any monitored parameter is significantly different (p<0.05) from animals in the same or other groups. The animals are disconnected from the ventilator after spontaneous breathing was observed and transferred to a heating pad until waking up. Each animal is housed in one cage individually, with free access to food and water. All histological, biochemical, and behavioral assessments in the study are performed blindly. This description applies to all animals and surgeries in this proposal.

Moderate LFP-Induced TBI

Experimental moderate LFP-TBI is produced using a fluid percussion device (VCU Biomedical Engineering)[63] in a lateral orientation[64]. Rats are anesthetized, intubated, and mounted in a stereotaxic frame, a midline scalp incision is made, and a 4.8-mm diameter craniotomy is performed with a trephine on the right parietal bone (4.5 mm posterior to bregma and 3.0 mm lateral to the sagittal suture). A rigid plastic injury tube (modified Luer-Loc needle hub, 2.6 mm inside diameter) is glued over the craniotomy with cyanoacrylate. The fluid percussion device consists of a Plexiglas cylindrical reservoir filled with isotonic saline. One end of the reservoir has a Plexiglas piston mounted on O-rings. The opposite end consists of a transducer housing ending with a 2.6-mm outer diameter male Luer-Loc. Brain injury is induced by the descent of the pendulum from a known height striking the piston of the saline-filled reservoir, forcing a fluid bolus (about 0.1 mL) into the closed cranial cavity and producing a brief displacement and deformation of brain tissue. After connecting the rats to the fluid percussion device via the Luer-Loc system, a fluid percussion pulse of 2.15 ATM is delivered to achieve moderate TBI. Sham controls are surgically prepared and treated identically but with no pressure pulse delivered to brain.

Intracardiac Blood Collection

The rats are anesthetized at 24 hr post-TBI. In addition to 2 mL blood being collected in a PAXgene tube for RNA, 6 mL blood is drawn into a syringe containing 600 μL sodium citrate via cardiac puncture from each rat. Blood in PAXgene tubes is used to examine miR-125b-5p in blood and detect gene expression in whole blood. Citrated blood is used to isolate leukocytes and platelets and detect miR-125b-5p targets by Western blots and RT-PCR in the individual blood cell types.

Total RNA Isolation, miR Array Assays, and Taqman Individual miR Assay

Total RNA (including miR) is isolated as described previously[28]. The concentration and integrity of the RNA is determined using a NanoDrop-1000 (Thermo Sci) and Agilent-2100 Bioanalyzer (Agilent). The miR arrays (Affymetrix) are employed to detect expression of miRs in blood after TBI. Partek Genomics Suite 6.4 is used to perform statistical analyses. ANOVA with a false discovery rate (FDR) of 0.05 to correct for multiple comparisons is used to examine the differentially expressed miRs in each group compared to others. A TaqMan miR-125b-5p assay (Life Tech) is employed to detect expression of miR-125b-5p using a 7900HT real-time PCR instrument (ABI). U6 is used as the endogenous control. Statistical differences are assessed using ANOVA followed by Dunnett's post hoc test.

Isolation of Leukocytes, Platelets, and Plasma from Whole Blood

The 6 mL citrated blood (sodium citrate: blood=1:10) collected from each rat is split into two parts: 4 ml for leukocyte isolation, and 2 ml for platelets and plasma isolation. We perform density gradient centrifugation to isolate leukocytes using the SepMate device (Stemcell Tech). After adding EDTA (final concentration at 5 mM) to the citrated blood, we centrifuge the blood sample at 120 g for 20 min at room temperature. After pipetting supernatant (platelet rich plasma, PRP) into a plastic tube, we centrifuge the PRP at 2,000 g for 10 min to deposit platelets, and pipette the supernatant (plasma) to a new tube. Platelets and leukocytes are frozen in liquid nitrogen and stored at −70° C. for RT-PCR and Western blot, and plasma is stored at −70° C. for Elisa/Western blots.

BBB Permeability and Brain Edema Measurements

Two dyes sodium fluorescein (NF) and Evans blue (EB) may be used to measure BBB permeability as previously described[19]. For NF/EB extravasation studies, rats are perfused through the carotids with Ringer's solution containing 1 g/L each of NF and EB for 5 min. Animals are decapitated and ipsilateral hemisphere is dissected and homogenized in 7.5% (w/v) trichloroacetic acid. Samples are measured by fluorimetry (excitation 485 nm, emission 538 nm) for NF and by absorbance spectroscopy at 620 nm for EB determination. Histological extent of edema is calculated using the Swanson method[83]. Statistical differences are determined using ANOVA with post hoc Bonferroni test.

Brain Tissue Collection

After blood is drawn, rats are perfused with intracardiac saline followed by either 4% paraformaldehyde (PFA) perfusion, or dissection of ipsilateral cortex. The PFA fixed brains are sucrose-protected (30%), and brain sections (50 μm) cut in a cryostat at −20° C., and used for immunohistochemistry. Dissected fresh brain is frozen in liquid nitrogen and stored at −70° C. for RT-PCR and Western blot.

Immunohistochemistry—Double Labeling of RECA1 and CD3

The fixed brain sections are double labeled with mouse anti-RECA1 (endothelial cell marker, 1:1,000, Serotec) and with rabbit anti-CD3 (T cell marker, 1:100, Abcam). Primary antibodies are incubated at room temperature (RT) for 1 hr in PBS containing 0.1% Triton X-100 and 3% serum of the species in which the secondary antibodies are raised. Species-specific IgGs, conjugated to Alexa 594 or 488 (1:1,000; Life Tech), are used as secondary antibodies. The CD3$^+$ cells in images from the brain parenchyma adjacent to TBI injury site are counted using optical dissector stereology, and statistical differences are assessed using ANOVA with post hoc Bonferroni test.

Assessment of Blood in Brain Following TBI

Several methods are used. Histologically, areas of blood stained tissue are quantified on every third section through the area of injury. Knowing the distances between tissue sections, a hemorrhage volume is calculated. Average hemorrhage volumes per group are calculated and differences between groups assessed using an ANOVA. In the other half of the animals, the entire hemisphere is homogenized and hemoglobin concentrations measured using Drabkins reagent and hemoglobin concentrations calculated from a standard curve.

Example 12—Define Therapeutic Window of miR-125b-5p Mimic after TBI

All experiments with the miR-125b-5p mimic described in Example 11 are duplicated in this experiment, except that animals are grouped differently due to miR-125b-5p mimic administered at different time points (1, 3, 6 hr) after TBI. Briefly, Sprague-Dawley adult rats of both sexes (n=80) are divided into 5 groups (each group of 16 rats including 2 sub-groups: 8 male, 8 female), including sham operation (Group 1), TBI rats injected with scrambled miR (dose from Example 11, i.v., given at 1 hr after TBI) (Group 2); TBI rats injected miR-125b-5p mimic (dose from Example 11, i.v., given at 1, 3, or 6 hr after TBI) (Groups 3-5).

Example 13—Measure the Long-Term Effects of miR-125b-5p Mimic after TBI

The TBI surgery performed in Example 11 is duplicated in this experiment. Instead of BBB permeability and brain edema measurements, the rats in this experiment are subjected to assessments in the Morris water maze from 11-15 days and hippocampal neuron survival at 16 days after TBI. Rats (n=48) are divided into 3 groups (each group of 16 rats including 2 sub-groups: 8 male, 8 female). The 3 groups include: sham (Group 1); TBI rats given miR scramble or miR-125b-5p mimic (dose from Example 11, i.v., given at 0 hr, Groups 2, 3).

Morris Water Maze

Spatial memory is assessed using the Morris water maze on 11 through 15 days after TBI in rats. The apparatus and methods are described in recent publications[20, 84]. In brief, rats are released from one of four starting points and allowed 120 s to find the escape platform. Rats receive a total of 4 trials per day, one from each starting point, over 5 consecutive days. Behavioral assessments are performed by an individual blinded to the treatment groups. Mean latency to find the platform is calculated for each day to assess learning as well as the mean swimming speed to assess motor function. Statistical differences are determined using repeated measures ANOVA followed by Dunnett's post hoc test.

Brain Sample Preparation and Immunohistochemistry—Labeling NeuN

The brain tissue collection and immunohistological staining are duplicated as described in Example 11, except that: (1) the animals are terminated after completing behavioral tests at 16 d after TBI; (2) different primary antibody and method are used to label hippocampal neurons. Briefly, brain sections are incubated in 0.3% $H_2O_2$ for 10 minutes to quench endogenous peroxidase, incubated with 3% horse blocking serum for 20 minutes, and then incubated overnight in primary antibody (mouse anti-NeuN, mature neuron marker, 1:150, Millipore), then in biotinylated secondary antibody (Goat anti-mouse 1:1,000, Vector) for 0.5 h, then placed in Vectastain ABC reagent for 0.5 h and incubated in peroxidase substrate 3, 3'-diaminobenzidine (DAB) solution for 10 min.

Stereological Cell Counts

The total number of NeuN-positive pyramidal neurons in the CA1, CA2, CA3, dentate gyrus and dentate hilus region of the hippocampus is quantified bilaterally using stereological methods as described previously[20]. The NeuN-positive cell counts are performed on a microscope (Nikon E600, Nikon) using commercial software (Stereo Investigator™8.0, Microbrightfield, Inc.). Serial sections cut at 50 μm thick are collected at Bregma −2.80 mm to Bregma −4.16 mm for a total of 10 sections per brain. Estimated numbers of the NeuN-positive neurons in the target brain region are generated by the Stereologer software using the following equation: $\Sigma N_{obj}=(\Sigma N)(1/SSF)(1/ASF)(1/TSF)^{85}$. In this equation $\Sigma N_{obj}$ indicates the sum of objects sampled in the sections, SSF indicates the section sampling fraction, ASF indicates the area sampling fraction, and TSF indicates the thickness sampling fraction. Counting is performed by a blinded observer. Statistical differences are determined using ANOVA followed by Dunnett's post hoc test.

It is expected that miR-125b-5p mimic will block T cell infiltration, decrease bleeding, decrease BBB permeability, reduce hippocampal neuron death, and prevent spatial memory deficits after TBI in rats. The protection will be dose related and will last at least 16 days. Should the 4.8 mg/kg dose in Example 14 below be significantly more effective than the 2.4 mg/kg dose, then higher doses will be tested to find the most effective dose. It is expected that the therapeutic time window will be from 0 to 6 hr after TBI, but longer times will be investigated if a 6 h treatment is very effective. The hormonal cycles in the female rats will be tracked and only use them on the proestrus day when estrogen levels are highest to show protection above that might be observed with estrogen.

Example 14—Profile the Expression of miR-125b-5p Target Genes in Blood after miR-125b-5p Mimic Treatment Following TBI This experiment demonstrates that administration of miR-125b-5p mimic after TBI markedly decreases the expression of three genes that are the best miR-125b-5p targets (i.e., Mknk2, Alpk3, Neu1) as predicted by TargetScanRat. Based on the miR-mRNA 3'UTRs principle of negative regulation[8-12], a database of more than 1,000 miR-125b-5p target genes was generated using miR-target gene algorithms (TargetScanRat). Due to the principle that an miR normally negatively regulates its target genes, the miR-125b-5p target genes, that are decreased following the treatment of miR- 125b-5p mimic after TBI, are more likely responsible to the therapeutic effects of miR-125b-5p to improve TBI outcomes. Given that inhibiting a single oncogene/kinase Src can improve multiple TBI outcome measurements[19-22], targeting miR-125b-5p to inhibit multiple target oncogenes/ kinases (e.g., Mknk2, Alpk3, Neu1) and their downstream oncogenes/kinases (including Src) might be more effective.

Each miR has a seed region that binds to complementary sequences in 3'UTR of its targets, resulting in negative regulation, such as transcript degradation or post-translational suppression[8-12]. The 3'UTR plasmids provide a convenient solution for quantitative assessment of the inhibitory effect between miRs and their target genes. Specifically, the interaction between miR and wild 3'UTR of its target gene would result in reduction of the luciferase activity, whereas the mutated 3'UTR does not. The chimeric transcript level is regulated by its interaction with miR(s), which results in varied luciferase activity quantifiable using a colorimetric assay.

To address which targets are responsible for the therapeutic effects of miR-125b-5p on TBI, in vivo Morpholino Oligos (MO) will be used, as they interfere with a single miR-mRNA pair by binding to the 3'UTR of target. Therefore, in vivo MOs can act as the "antagonists" to specifically compete with miR-125b-5p for binding sites within 3'UTR of each individual miR-125b-5p target. For example, the MO designed to compete with miR-125b-5p for 3'UTR of Alpk3 (MO-miR-125b-5p-Alpk3) is able to block the recognition/binding of miR-125b-5p to Alpk3.

The total RNAs (including miRs) isolated from blood samples described in the experiments for Example 11 may be used for this experiment.

Whole Genome Microarray Assays of Gene Expression in Whole Blood

Rat whole genome MicroArrays (Affymetrix) are employed to detect altered genes after miR-125b-5p mimic treatment after TBI. Partek Genomics Suite 6.4 is used to perform statistical analyses. ANOVA with false discovery rate (FDR) of 0.05 correction for multiple comparisons is used to examine the differentially expressed mRNAs in each group compared to the others.

Integrated miR-125b-5p, Altered mRNA Network and Functional Analyses

The integrated functional network analyses of miR-125b-5p and altered mRNAs will be performed according to methods described previously[86]. Briefly, the list of significantly down-regulated mRNAs, and a database of miR-125b-5p target genes will be uploaded into the integrated miR-mRNA functional network analyses software: Exploratory Gene Association Networks (EGAN). The integrated miR-125b-5p and target genes functional networks will be identified and subjected to functional analysis using the Kyoto Encyclopedia of Genes and Genomes (KEGG). This network analysis will lead to the responsive target genes that miR-125b-5p works on.

Assessment of miR-125b-5p Targets Using RT-PCR and Western Blots in Platelets and Leukocytes RT-PCR and Western blot analyses are performed using published protocols[20]. Briefly, total RNA and protein are extracted from platelets and leukocytes using mirVana PARIS kit (Ambion). Reagents and primers specific for Mknk2, Alpk3, and Neu1 have been purchased from Life Tech and standard Taqman RT-PCR protocol followed. Proteins are detected with antibodies, including rabbit anti-rat Mknk2 (1:500, abcam), rabbit anti-rat Alpk3 (1:500, Aviva), and rabbit anti-rat Neu1 (1:500, Aviva). Bands on membranes are visualized using LI-COR imaging system (LI-COR), and quantified by optical density methods using the ImageJ. 18S mRNA and GAPDH protein are used as internal controls for RT-PCR and Western blots, respectively. Statistical differences are determined using unpaired t-test.

Immunohistochemistry-Double Labeling for RECA1 with miR-125b-5p Targets in Endothelium The immunostaining described in Example 11 is duplicated here. In addition to RECA-1, additional primary antibodies include rabbit anti-rat Mknk2 (1:200, Abcam), rabbit anti-rat Alpk3 (1:200, Aviva), and rabbit anti-rat Neu1 (1:100, Aviva). The immunostained images are quantified using ImageJ, and statistical differences are determined using ANOVA with post hoc Bonferroni test.

Example 15—Confirm the Binding Sites of miR-125b-5p on Target Genes (Mknk2, Alpk3, Neu1)

This experiment demonstrates Morpholino Oligos (MO) to each of the three miR-125b-5p target mRNAs blocks the binding of miR-125b-5p to each of the three targets genes in vitro. Luciferase reporter assay and cell permeable antisense MO in vitro assay are used to confirm the binding sites of miR-125b-5p on target genes (Mknk2, Alpk3, Neu1).

Oligonucleotides and DNA Constructs

Full length rat Mknk2, Alpk3, and Neu1 (wild-type and mutant) 3'UTR are synthesized and cloned into the firefly luciferase reporter vector pMirTarget (OriGene). The mutant 3'UTR luciferase plasmid is created by mutating miR-125b-5p seed-match sequences, according to the alignment between miR-125b-5p and these genes (FIG. 2). For example, nucleotides 413-419 (5'-tctagccttgtgactCTCAGGGt-3' (SEQ ID NO:5)) of Alpk3 3'UTR contain the predicted miR-125b-5p seed-match sequences. The mutated nucleotides are (5'-tGAGACT-Caccctaacttgtga-3' (SEQ ID NO:6)) (highlighted in bold). Both wild-type and mutant inserts are synthesized and confirmed by OriGene.

Target Protector Vivo-Morpholino Oligos (MO) Constructs

Figure 16:
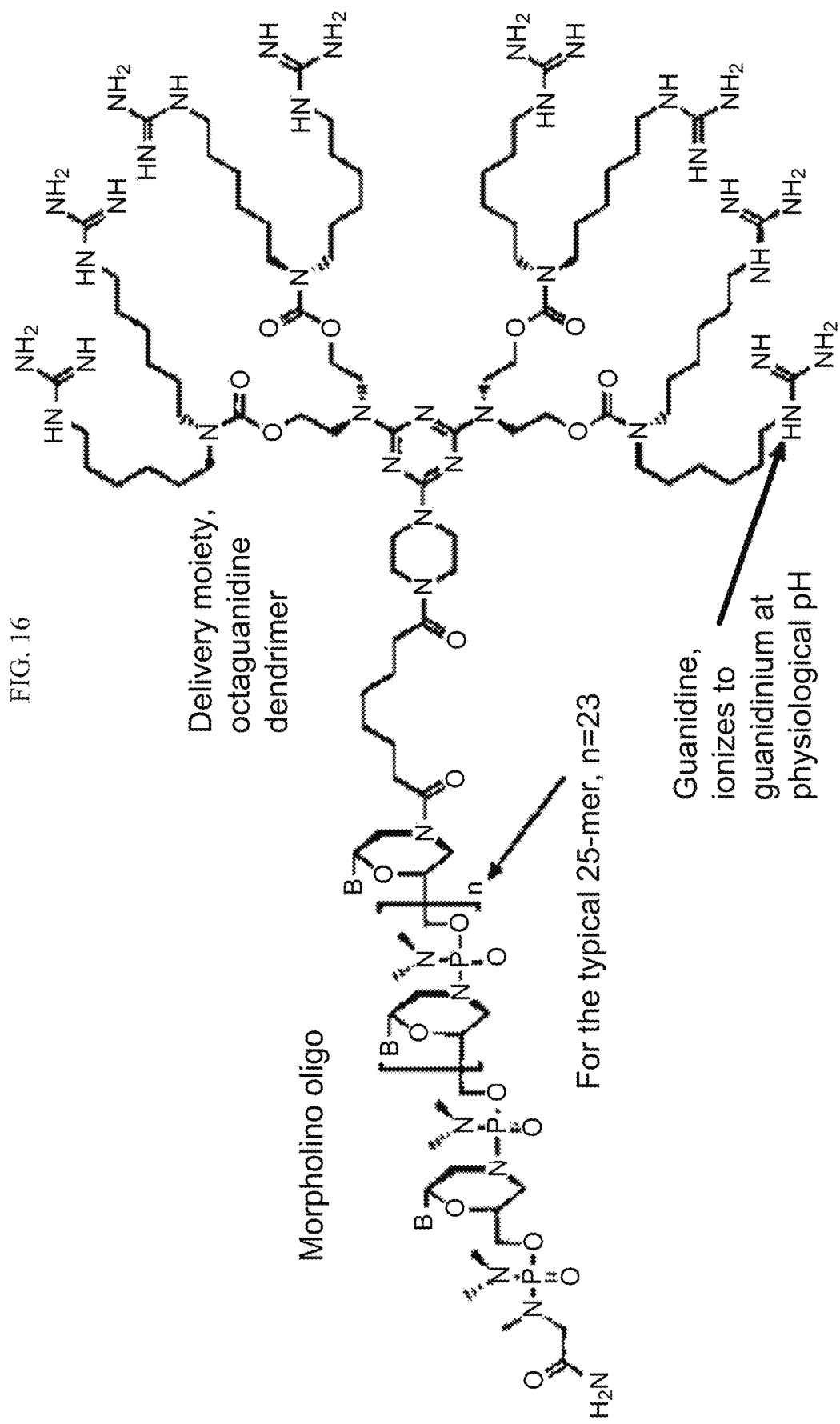
FIG. 16 shows the structure of anti-sense Morpholino Oligos (MO).

The MO (FIG. 16) sequences of Mknk2, Alpk3, and Neu1 are designed based on the alignment between miR-125b-5p and these genes (FIG. 2) using the DNA Software (Gene Tools). The software includes a formula for predicting melting temperature to indicate MO-RNA affinity. Different MOs were constructed and the best one that was not only predicted with little self-complementarity but also validated with high affinity to each target gene using the 3'UTR luciferase reporter assay was chosen. As an example for MO-miR-125b-5p-Mknk2, one 19 base MO (CAGGCT-GAGCCCTGAGAAG (SEQ ID NO:3)) and one 20 base MO (GTCAGGCTGAGCCCTGAGAA (SEQ ID NO:4)) were constructed. For another example, MO-miR-125b-5p-Alpk3 nucleotides are (5'-tGTGACTCtcagtgttccgatct-3' (SEQ ID NO:7)), complementary to the nucleotides 413-419 (5'-tctagccttgtgactCTCAGGGt-3' (SEQ ID NO:5)) in Alpk3 3'UTR. One mismatch is designed for MO-miR-125b-5p-Alpk3 to reduce G content, as high G content decreases the MO's aqueous solubility. Then, the nucleotides are synthesized and coupled with the vivo-delivery moiety that is comprised of an octaguanidine dendrimer (Gene Tools) (FIG. 16). In addition, MO uses active component of arginine rich delivery peptides (guanidinium group) to improve the stability (FIG. 16). We use MO at 500 nM and 1000 nM (these doses are 10-20 times than miR mimic used in luciferase assay, and do not affect cell viability) to assure that MO saturates binding sites of target genes. There are no safety problems of using MOs in vitro, and has no cell toxicity. In addition, MO is stable, water soluble and cell permeable, meeting all requirements for in vitro use.

Cells and Transfection and Luciferase Reporter Assays

Neuro2a cells (ATCC, derived from male mice) are cultured in EMEM supplemented with 10% FBS (Gibco) and 100 µg/mL penicillin/streptomycin. Neuro2a cells are seeded at a density of $1 \times 10^5$ cells/well in a 24-well plate one day before transfection. Cells are co-transfected with either 0.5 µg pMirTarget 3'UTR reporter (wild) or pMirTarget 3'UTR reporter (mutant) clones validation (OriGene), transfection internal control 5 ng hRluc-TK (Promega), and scramble miR, or 50 nM miR-125b-5p mimic or MO-target of miR-125b-5p using Lipofectamine 3000 (Life Tech) according to the vendor's protocol. The luciferase reporter assays are performed as described[31]. The wild or mutated target gene, such as Alpk3, 3'UTR clone is constructed downstream of the firefly luciferase gene. The chimeric transcript level is regulated by its interaction with miR, which causes varied luciferase activity quantifiable by a colorimetric assay. Cells are harvested at 48 h after transfection, and firefly luciferase and control renilla luciferase activity measured in lysates using the firefly luciferase assay kit (Biotium) and renilla luciferase assay kit (Biotium) with a Beckman Luminometer. Results from triplicate experiments are displayed as a ratio of firefly/Renilla luciferase activity, expressed as a percentage of values obtained in cells treated with scramble miR. Statistical differences are determined using ANOVA with post hoc Bonferroni test.

Example 16—Effects of MO to Each of the Three miR-125b-5p Target mRNAs

This experiment determines if in vivo MO to each of the three miR-125b-5p target mRNAs prevents the decrease of targets in leukocytes and endothelium produced by miR-125b-5p mimic, and blocks the beneficial effects of miR-125b-5p mimic on TBI outcomes. The TBI surgery performed in Example 11 is duplicated here, except that animals are grouped due to different MO treatments. Briefly, the MO (12 mg/kg, i.v.) specific to each miR-125b-5p target is administered 15 min prior to TBI followed by miR-125b-5p mimic (2.4 mg/kg, i.v.) injection immediately after TBI. Rats of both sexes (n=96) are divided into 6 groups (each group of 16 rats including 2 sub-groups: 8 male, 8 female), including sham operation (Group 1), TBI rats injected scrambled miR, or miR-125b-5p mimic (Groups 2-3); TBI rats injected MO to three targets followed by miR-125b-5p mimic (Groups 4-6). The experimental sample collection (fresh blood, and fixed brain), blood cell isolation, immunostaining, Western blot, and data analyses described in Example 11 are duplicated here. In the pilot study, in vivo MO doses of 12 mg/kg are used, which are 5 times higher than the dose of miR-125b-5p mimic and administer the MO i.v. at least 15 min prior to miR mimic treatment to assure that MO saturates miR binding sites of target genes in vivo.

It is expected that the MO to each one of the three miR-125b-5p targets (Mknk2, Alpk3, Neu1) blocks the decrease of the target gene (in blood cells and endothelium) and decreases the beneficial effects produced by miR-125b-5p mimic after TBI in rats. Along with the broad therapeutic effects, potential off-target effects of miR therapeutics exist as a concern in the field[46, 47], as the miR may also regulate the other genes irrelevant to TBI outcome with potential negative effects. This problem could be solved by the in vivo MOs that are specific to the miR-target pairs to reduce the side effects. Another potential problem is the high G content (>36%) would decrease the aqueous solubility of a MO. If this is the case, a mismatch of a few nucleotides can be introduced to reduce G content, but have little impact on its ability to block miR-target recognition/interaction. It is possible that miR-125b-5p exerts its effects by acting on multiple target genes at once. To address this possibility, animals may be infused with all three MO at once prior to giving miR-125b-5p to see if this has a greater effect. In addition, other genes (e.g., Map3K10, Tjap1, Mapre2, Asb13, Zdhhc9, DNAjb5, and Bmpr2; FIG. 12) that are decreased in blood by miR-125b-5p mimic will be studied. Future studies will be performed with collaborators on a gyrencephalic mammal such as the ferret with different seventies and types of injury.

Example 17—Statistical Analyses, Sample Size/Power Estimate, and Study Design

Statistical analyses of behavioral and histological experiments are based on a repeated measures ANOVA, or ANOVA with post hoc Bonferroni test. To evaluate power of the proposed experiments, some simplifying assumptions were made. Experiments planned generally have 8 subjects per group (males and females are assumed to be different groups). Assuming a two-group comparison using 8 subjects per group, and assuming the total degrees of freedom from the ANOVA are such that a Z score could be used, 90% power is available to detect differences 1.6 times the standard deviation using an alpha of 0.05. A Kolmogorov-Smirnov test is done to see if data are non-parametric. If they are, then a Mann-Whitney U test is used to compare two groups, and a Kruskal-Wallis one-way analysis of variance by ranks used to compare 3 or more groups. A $P<0.05$ is considered significant after a Bonferroni correction for multiple comparisons. Behavioral, histological, and biochemical analyses are performed and analyzed by individuals blinded to the treatment groups. Animals are randomized to treatment groups prior to an experiment.

Example 18—Summary of Experimental Results

The time course data showed miR-125b-5p decreased over 10 fold at 24 hr and resolved gradually over time after TBI (FIG. 4A). This mirrors the time course of T cell infiltration that peaked at 24 hr after TBI (FIGS. 5A-5O). The similar time course suggests that decrease of tumor suppressor miR-125b-5p in blood might be associated with T cell infiltration after TBI. Indeed, the data showed that intravenous (i.v.) miR-125b-5p mimic (2.4 mg/kg, i.v. given at 0 hr) significantly elevated miR-125b-5p in blood (FIG. 6) and blocked T cell infiltration following TBI, as well as reduced bleeding, endothelial cell loss (FIGS. 7A-7L), and hippocampal neuron loss (FIGS. 8A-8F). Using whole genome microarrays, it was shown that miR-125b-5p mimic (2.4 mg/kg, i.v. given at 0 hr) significantly suppressed numerous genes in blood 24 hr after TBI in rats, among which were oncogenes/kinases (e.g., Mknk2, Alpk3, Neu1, Src, and others) and inflammatory genes (e.g., Il12rb2, Bmpr2, and others) ($P<0.05$, Fold change$<-1.2$) (FIG. 10). Using the computational miRanda algorithm (TargetScan-Rat) and Exploratory Gene Association Networks (EGAN), numerous miR-125b-5p target genes (e.g., Mknk2, Alpk3, Neu1, Map3k10, Tjap1, Rpusd2, and others) that were predicted to be direct targets of miR-125b-5p were identified. The networks of miR-125b-5p, miR-125b-5p targets, and other related downstream genes that were decreased in blood by miR-125b-5p mimic treatment 24 hr post-TBI are also shown (FIG. 11).

Using a stringent cut-off (CS score<−0.75 in targetscan.org), the mechanistic studies were focused on three miR-125b-5p targets (Mknk2, Alpk3, and Neu1) (FIGS. 11 and 12) that are mostly novel to TBI. Methods to study miR-target recognition/interaction, including constructs of wild-type and mutant 3′UTR luciferase plasmid, and constructs of MO that are able to compete with miR drug for binding sites in 3′UTR of miR targets in vitro and in vivo, were established (FIGS. 13, 14, and 15A-15C). For example, the MO designed to compete with miR-125b-5p for 3′UTR of Mknk2 (MO-miR-125b-5p-Mknk2) can block the recognition/binding of miR-125b-5p to Mknk2. The miR-125b-5p target binding study data showed that miR-125b-5p (50 nM) decreased luciferase activity of 3′UTR clones of Mknk2 and Neu1, respectively (P<0.01 vs. 3′UTR clone/miR-scramble) (FIG. 18). The miR-125b-5p target binding study data also showed that in vitro MO-miR-125b-5p-Mknk2 (19 bases, CAGGCTGAGCCCTGAGAAG (SEQ ID NO:3)) (500 nM) prevented miR125b-5p-induced decrease of luciferase activity of Mknk2 3′UTR clone, whereas MO-miR-125b-5p-Mknk2 (20 bases, GTCAGGCTGAGCCCTGAGAA (SEQ ID NO:4)) (500 nM) had little effects. (P<0.01 vs. Mknk2 3′UTR/miR-scramble; P<0.01 vs. Mknk2 3′UTR/miR-125b-5p) (FIG. 19).

Exemplary Embodiments

Exemplary embodiments provided in accordance with the presently disclosed subject matter include, but are not limited to, the claims and the following embodiments:

1. A method for treating a brain injury in a subject, the method comprising administering to the subject a therapeutically effective amount of a microRNA (miR) or a mimic thereof, wherein the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2.

2. The method of embodiment 1, wherein the miR or the mimic thereof decreases the expression level of at least one gene selected from the group consisting of Mknk2, Alpk3, and Neu1.

3. The method of embodiment 1 or 2, wherein the expression level is decreased at least 1.5 fold relative to the expression level of the gene prior to the administration of the miR or the mimic thereof.

4. The method of any one of embodiments 1 to 3, wherein the miR is selected from the group consisting of miR-125b-5p, miR-122-5p, and a combination thereof.

5. A method for treating a brain injury in a subject, the method comprising administering to the subject a therapeutically effective amount of a microRNA (miR) or a mimic thereof, wherein the miR is selected from the group consisting of miR-125b-5p, miR-122-5p, and a combination thereof.

6. The method of embodiment 5, wherein the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2.

7. The method of embodiment 6, wherein the miR or the mimic thereof decreases the expression level of at least one gene selected from the group consisting of Mknk2, Alpk3, and Neu1.

8. The method of embodiment 6 or 7, wherein the expression level is decreased at least 1.5 fold relative to the expression level of the gene prior to the administration of the miR or the mimic thereof.

9. The method of any one of embodiments 4 to 8, wherein the miR-125b-5p comprises a nucleotide sequence having at least 90% sequence identity to UCCCUGAGACCCUAACUUGUGA (SEQ ID NO:1).

10. The method of any one of embodiments 4 to 8, wherein the miR-122-5p comprises a nucleotide sequence having at least 90% sequence identity to UGGAGUGUGACAAUGGUGUUUG (SEQ ID NO:2).

11. A method for preventing or reducing neuronal death after a brain injury in a subject, the method comprising administering to the subject a therapeutically effective amount of a microRNA (miR) or a mimic thereof, wherein the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2.

12. The method of embodiment 11, wherein the miR or the mimic thereof decreases the expression level of at least one gene selected from the group consisting of Mknk2, Alpk3, and Neu1.

13. The method of embodiment 11 or 12, wherein the expression level is decreased at least 1.5 fold relative to the expression level of the gene prior to the administration of the miR or the mimic thereof.

14. The method of any one of embodiments 11 to 13, wherein the miR is selected from the group consisting of miR-125b-5p, miR-122-5p, and a combination thereof.

15. A method for preventing or reducing neuronal death after a brain injury in a subject, the method comprising administering to the subject a therapeutically effective amount of a microRNA (miR) or a mimic thereof, wherein the miR is selected from the group consisting of miR-125b-5p, miR-122-5p, and a combination thereof.

16. The method of embodiment 15, wherein the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2.

17. The method of embodiment 16, wherein the miR or the mimic thereof decreases the expression level of at least one gene selected from the group consisting of Mknk2, Alpk3, and Neu1.

18. The method of embodiment 16 or 17, wherein the expression level is decreased at least 1.5 fold relative to the expression level of the gene prior to the administration of the miR or the mimic thereof.

19. The method of any one of embodiments 14 to 18, wherein the miR-125b-5p comprises a nucleotide sequence having at least 90% sequence identity to UCCCUGAGACCCUAACUUGUGA (SEQ ID NO:1).

20. The method of any one of embodiments 14 to 18, wherein the miR-122-5p comprises a nucleotide sequence having at least 90% sequence identity to UGGAGUGUGACAAUGGUGUUUG (SEQ ID NO:2).

21. A method for preventing or reducing leukocyte infiltration after a brain injury in a subject, the method comprising administering to the subject a therapeutically effective amount of a microRNA (miR) or a mimic thereof, wherein the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2.

22. The method of embodiment 21, wherein the miR or the mimic thereof decreases the expression level of at least one gene selected from the group consisting of Mknk2, Alpk3, and Neu1.

23. The method of embodiment 21 or 22, wherein the expression level is decreased at least 1.5 fold relative to the expression level of the gene prior to the administration of the miR or the mimic thereof.

24. The method of any one of embodiments 21 to 23, wherein the miR is selected from the group consisting of miR-125b-5p, miR-122-5p, and a combination thereof.

25. A method for preventing or reducing leukocyte infiltration after a brain injury in a subject, the method comprising administering to the subject a therapeutically effective amount of a microRNA (miR) or a mimic thereof, wherein the miR is selected from the group consisting of miR-125b-5p, miR-122-5p, and a combination thereof.

26. The method of embodiment 25, wherein the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2.

27. The method of embodiment 26, wherein the miR or the mimic thereof decreases the expression level of at least one gene selected from the group consisting of Mknk2, Alpk3, and Neu1.

28. The method of embodiment 26 or 27, wherein the expression level is decreased at least 1.5 fold relative to the expression level of the gene prior to the administration of the miR or the mimic thereof.

29. The method of any one of embodiments 24 to 28, wherein the miR-125b-5p comprises a nucleotide sequence having at least 90% sequence identity to UCCCUGAGACCCUAACUUGUGA (SEQ ID NO:1).

30. The method of any one of embodiments 24 to 28, wherein the miR-122-5p comprises a nucleotide sequence having at least 90% sequence identity to UGGAGUGUGACAAUGGUGUUUG (SEQ ID NO:2).

31. A method for preventing or reducing blood-brain barrier (BBB) disruption after a brain injury in a subject, the method comprising administering to the subject a therapeutically effective amount of a microRNA (miR) or a mimic thereof, wherein the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2.

32. The method of embodiment 31, wherein the miR or the mimic thereof decreases the expression level of at least one gene selected from the group consisting of Mknk2, Alpk3, and Neu1.

33. The method of embodiment 31 or 32, wherein the expression level is decreased at least 1.5 fold relative to the expression level of the gene prior to the administration of the miR or the mimic thereof.

34. The method of any one of embodiments 31 to 33, wherein the miR is selected from the group consisting of miR-125b-5p, miR-122-5p, and a combination thereof.

35. A method for preventing or reducing blood-brain barrier (BBB) disruption after a brain injury in a subject, the method comprising administering to the subject a therapeutically effective amount of a microRNA (miR) or a mimic thereof, wherein the miR is selected from the group consisting of miR-125b-5p, miR-122-5p, and a combination thereof.

36. The method of embodiment 35, wherein the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2.

37. The method of embodiment 36, wherein the miR or the mimic thereof decreases the expression level of at least one gene selected from the group consisting of Mknk2, Alpk3, and Neu1.

38. The method of embodiment 35 or 36, wherein the expression level is decreased at least 1.5 fold relative to the expression level of the gene prior to the administration of the miR or the mimic thereof.

39. The method of any one of embodiments 34 to 38, wherein the miR-125b-5p comprises a nucleotide sequence having at least 90% sequence identity to UCCCUGAGACCCUAACUUGUGA (SEQ ID NO:1).

40. The method of any one of embodiments 34 to 38, wherein the miR-122-5p comprises a nucleotide sequence having at least 90% sequence identity to UGGAGUGUGACAAUGGUGUUUG (SEQ ID NO:2).

41. The method of any one of embodiments 1 to 40, wherein the brain injury is an acute brain injury.

42. The method of embodiment 41, wherein the acute brain injury is selected from the group consisting of traumatic brain injury (TBI), concussion, intracerebral hemorrhage (ICH), intraventricular hemorrhage (IVH), subarachnoid hemorrhage (SAH), seizure, and ischemic stroke.

43. The method of any one of embodiments 1 to 42, wherein the brain injury is caused by a fall, an assault, a motor vehicle accident, a sport or recreational injury, shaken baby syndrome, a gunshot wound, a combat injury, a stroke, an infectious disease, a seizure, an electric shock, a tumor, a toxic exposure, a neurotoxic poisoning, a lack of oxygen, or a drug overdose.

44. The method of embodiment 43, wherein the infectious disease is meningitis or encephalitis.

45. The method of embodiment 43, wherein the neurotoxic poisoning is carbon monoxide poisoning or lead poisoning.

46. The method of any one of embodiments 1 to 45, wherein the miR or the mimic thereof is administered to the subject intravenously, intramuscularly, orally, intradermally, subcutaneously, intraarterially, intraperitoneally, intralesionally, intracranially, intraarticularly, intraprostatically, intrapleurally, intratracheally, intranasally, intravitreally, intravaginally, intrarectally, topically, intratumorally, subconjunctival, intravesicularlly, intrapericardially, intraumbilically, or intraocularally.

47. The method of embodiment 46, wherein the miR or the mimic thereof is administered to the subject intravenously.

48. The method of any one of embodiments 1 to 47, wherein the miR or the mimic thereof is administered using a nanoparticle.

49. The method of embodiment 48, wherein the miR or the mimic thereof is encapsulated in the nanoparticle.

50. The method of embodiment 49, wherein the nanoparticle is a liposome.

51. The method of embodiment 50, wherein the liposome is a polyethylene glycol (PEG) liposome.

52. The method of any one of embodiments 1 to 51, wherein the subject is a human.

53. A pharmaceutical composition comprising a microRNA (miR) or a mimic thereof and a pharmaceutically acceptable carrier, wherein the miR is selected from the group consisting of miR-125b-5p, miR-122-5p, and a combination thereof.

54. The pharmaceutical composition of embodiment 53, wherein the miR or the mimic thereof is encapsulated in a nanoparticle.

55. The pharmaceutical composition of embodiment 54, wherein the nanoparticle is a liposome.

56. The pharmaceutical composition of embodiment 55, wherein the liposome is a polyethylene glycol (PEG) liposome.

57. A kit comprising a microRNA (miR) or a mimic thereof and a nanoparticle, wherein the miR is selected from the group consisting of miR-125b-5p, miR-122-5p, and a combination thereof.

58. The kit of embodiment 57, wherein the miR or the mimic thereof and the nanoparticle are provided in separate containers or compartments.

59. The kit of embodiment 57, wherein the miR or the mimic thereof is encapsulated in the nanoparticle.

60. The kit of any one of embodiments 57 to 59, wherein the nanoparticle is a liposome.

61. The kit of embodiment 60, wherein the liposome is a polyethylene glycol (PEG) liposome.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described. All publications, patents, and patent applications cited in this specification are herein incorporated by reference as if each individual publication, patent, or patent application were specifically and individually indicated to be incorporated by reference.

REFERENCES

1. Faul, M., Xu, L., Wald, M. M., and Coronado, V. G. Traumatic brain injury in the United States: emergency department visits, hospitalizations, and deaths. Atlanta (Ga.): Centers for Disease Control and Prevention, National Center for Injury Prevention and Control. 7-23 (2010).
2. Maas, A. I., Roozenbeek, B., and Manley, G. T. Clinical trials in traumatic brain injury: past experience and current developments. *Neurotherapeutics* 7, 115-126 (2010).
3. Narayan, R. K., Michel, M. E., Ansell, B., Baethmann, A., Biegon, A., Bracken, M. B., Bullock, M. R., Choi, S. C., Clifton, G. L., Contant, C. F., Coplin, W. M., Dietrich, W. D., Ghajar, J., Grady, S. M., Grossman, R. G., Hall, E. D., Heetderks, W., Hovda, D. A., Jallo, J., Katz, R. L., Knoller, N., Kochanek, P. M., Maas, A. I., Majde, J., Marion, D. W., Marmarou, A., Marshall, L. F., McIntosh, T. K., Miller, E., Mohberg, N., Muizelaar, J. P., Pitts, L. H., Quinn, P., Riesenfeld, G., Robertson, C. S., Strauss, K. I., Teasdale, G., Temkin, N., Tuma, R., Wade, C., Walker, M. D., Weinrich, M., Whyte, J., Wilberger, J., Young, A. B., and Yurkewicz, L. Clinical trials in head injury. *J Neurotrauma* 19, 503-557 (2002).
4. Margulies, S., and Hicks, R. Combination therapies for traumatic brain injury: prospective considerations. *J Neurotrauma* 26, 925-939 (2009).
5. Schmidt, M. F. Drug target miRNAs: chances and challenges. *Trends Biotechnol* 32, 578-585 (2014).
6. Betel, D., Koppal, A., Agius, P., Sander, C., and Leslie, C. Comprehensive modeling of microRNA targets predicts functional non-conserved and non-canonical sites. *Genome Biol* 11, R90 (2010).
7. Li, Y., and Zhang, Z. Computational Biology in microRNA. *Wiley Interdiscip Rev RNA* 6, 435-452 (2015).
8. Bartel, D. P. MicroRNAs: genomics, biogenesis, mechanism, and function. *Cell* 116, 281-297 (2004).
9. Bartel, D. P. MicroRNAs: target recognition and regulatory functions. Cell 136, 215-233 (2009).
10. Jakymiw, A., Pauley, K. M., Li, S., Ikeda, K., Lian, S., Eystathioy, T., Satoh, M., Fritzler, M. J., and Chan, E. K. The role of GW/P-bodies in RNA processing and silencing. *J Cell Sci* 120, 1317-1323 (2007).
11. Wu, L., Fan, J., and Belasco, J. G. MicroRNAs direct rapid deadenylation of mRNA. *Proc Natl Acad Sci USA* 103, 4034-4039 (2006).
12. Lim, L. P., Lau, N. C., Garrett-Engele, P., Grimson, A., Schelter, J. M., Castle, J., Bartel, D. P., Linsley, P. S., and Johnson, J. M. Microarray analysis shows that some microRNAs downregulate large numbers of target mRNAs. *Nature* 433, 769-773 (2005).
13. Liu, D. Z., and Ander, B. P. Cell cycle phase transitions: signposts for aberrant cell cycle reentry in dying mature neurons. *Journal of Cytology & Histology* 2, e101 (2011).
14. Liu, D. Z., and Ander, B. P. Cell cycle inhibition without disruption of neurogenesis is a strategy for treatment of aberrant cell cycle diseases: an update. *ScientificWorldJournal* 2012, 491737 (2012).
15. Liu, D. Z. Repurposing cancer drugs to treat neurological diseases—Src inhibitors as examples. *Neural Regen Res* 12, 910-911 (2017).
16. Summy, J. M., and Gallick, G. E. Src family kinases in tumor progression and metastasis. *Cancer Metastasis Rev* 22, 337-358 (2003).
17. Matsuoka, T., and Yashiro, M. Rho/ROCK signaling in motility and metastasis of gastric cancer. *World J Gastroenterol* 20, 13756-13766 (2014).
18. Shi, Y., Zhang, L., Pu, H., Mao, L., Hu, X., Jiang, X., Xu, N., Stetler, R. A., Zhang, F., Liu, X., Leak, R. K., Keep, R. F., Ji, X., and Chen, J. Rapid endothelial cytoskeletal reorganization enables early blood-brain barrier disruption and long-term ischaemic reperfusion brain injury. *Nat Commun* 7, 10523 (2016).
19. Liu, D. Z., Ander, B. P., Xu, H., Shen, Y., Kaur, P., Deng, W., and Sharp, F. R. Blood-brain barrier breakdown and repair by Src after thrombin-induced injury. *Ann Neurol* 67, 526-533 (2010).
20. Liu, D., Sharp, F. R., Van, K. C., Ander, B. P., Ghiasvand, R., Zhan, X., Stamova, B., Jickling, G. C., and Lyeth, B. G. Inhibition of Src Family Kinases Protects Hippocampal Neurons and Improves Cognitive Function after Traumatic Brain Injury. *J Neurotrauma* 31, 1268-1276 (2014).

21. Liu, D. Z., Cheng, X. Y., Ander, B. P., Xu, H., Davis, R. R., Gregg, J. P., and Sharp, F. R. Src kinase inhibition decreases thrombin-induced injury and cell cycle re-entry in striatal neurons. *Neurobiol Dis* 30, 201-211 (2008).
22. Liu, D. Z., Waldau, B., Ander, B. P., Zhan, X., Stamova, B., Jickling, G. C., Lyeth, B. G., and Sharp, F. R. Inhibition of Src family kinases improves cognitive function after intraventricular hemorrhage or intraventricular thrombin. *J Cereb Blood Flow Metab* (2016).
23. Banzhaf-Strathmann, J., and Edbauer, D. Good guy or bad guy: the opposing roles of microRNA 125b in cancer. *Cell Commun Signal* 12, 30 (2014).
24. Hydbring, P., and Badalian-Very, G. Clinical applications of microRNAs. *F1000Res* 2, 136 (2013).
25. Chen, K., and Rajewsky, N. The evolution of gene regulation by transcription factors and microRNAs. *Nat Rev Genet* 8, 93-103 (2007).
26. Filip, A. MiRNA—new mechanisms of gene expression control]. *Postepy Biochem* 53, 413-419 (2007).
27. Liu, D. Z., Tian, Y., Ander, B. P., Xu, H., Stamova, B. S., Zhan, X., Turner, R. J., Jickling, G., and Sharp, F. R. Brain and blood microRNA expression profiling of ischemic stroke, intracerebral hemorrhage, and kainate seizures. *J Cereb Blood Flow Metab* 30, 92-101 (2010).
28. Jickling, G. C., Ander, B. P., Zhan, X., Noblett, D., Stamova, B., and Liu, D. microRNA expression in peripheral blood cells following acute ischemic stroke and their predicted gene targets. *PLoS One* 9, e99283 (2014).
29. Yin, K. J., Deng, Z., Huang, H., Hamblin, M., Xie, C., Zhang, J., and Chen, Y. E. miR-497 regulates neuronal death in mouse brain after transient focal cerebral ischemia. *Neurobiol Dis* 38, 17-26 (2010).
30. Selvamani, A., Sathyan, P., Miranda, R. C., and Sohrabji, F. An antagomir to microRNA Let7f promotes neuroprotection in an ischemic stroke model. *PLoS One* 7, e32662 (2012).
31. Ouyang, Y. B., Lu, Y., Yue, S., Xu, L. J., Xiong, X. X., White, R. E., Sun, X., and Giffard, R. G. miR-181 regulates GRP78 and influences outcome from cerebral ischemia in vitro and in vivo. *Neurobiol Dis* 45, 555-563 (2012).
32. Wang, P., Liang, J., Li, Y., Li, J., Yang, X., Zhang, X., Han, S., and Li, S. Down-regulation of miRNA-30a alleviates cerebral ischemic injury through enhancing beclin 1-mediated autophagy. *Neurochem Res* 39, 1279-1291 (2014).
33. Xu, L., Ouyang, Y., Xiong, X., Stary, C. M., and Giffard, R. G. Post-stroke treatment with miR-181 antagomir reduces injury and improves long-term behavioral recovery in mice after focal cerebral ischemia. *Exp Neurol* 264C, 1-7 (2014).
34. Shi, H., Sun, B. L., Zhang, J., Lu, S., Zhang, P., Wang, H., Yu, Q., Stetler, R. A., Vosler, P. S., Chen, J., and Gao, Y. miR-15b suppression of Bcl-2 contributes to cerebral ischemic injury and is reversed by sevoflurane preconditioning. *CNS Neurol Disord Drug Targets* 12, 381-391 (2013).
35. Peng, Z., Li, J., Li, Y., Yang, X., Feng, S., and Han, S. Downregulation of miR-181b in mouse brain following ischemic stroke induces neuroprotection against ischemic injury through targeting heat shock protein A5 and ubiquitin carboxyl-terminal hydrolase isozyme L1. *J Neurosci Res* 91, 1349-1362 (2013).
36. Zhao, H., Tao, Z., Wang, R., Liu, P., Yan, F., Li, J., Zhang, C., Ji, X., and Luo, Y. MicroRNA-23a-3p attenuates oxidative stress injury in a mouse model of focal cerebral ischemia-reperfusion. *Brain Res* 1592, 65-72 (2014).
37. Chi, W., Meng, F., Li, Y., Li, P., Wang, G., Cheng, H., Han, S., and Li, J. Impact of microRNA-134 on neural cell survival against ischemic injury in primary cultured neuronal cells and mouse brain with ischemic stroke by targeting HSPA12B. *Brain Res* 1592, 22-33 (2014).
38. Stary, C. M., Xu, L., Sun, X., Ouyang, Y. B., White, R. E., Leong, J., Li, J., Xiong, X., and Giffard, R. G. MicroRNA-200c Contributes to Injury From Transient Focal Cerebral Ischemia by Targeting Reelin. *Stroke* 46, 551-556 (2015).
39. Liu, P., Zhao, H., Wang, R., Wang, P., Tao, Z., Gao, L., Yan, F., Liu, X., Yu, S., Ji, X., and Luo, Y. MicroRNA-424 Protects Against Focal Cerebral Ischemia and Reperfusion Injury in Mice by Suppressing Oxidative Stress. *Stroke* 46, 513-519 (2015).
40. Xin, H., Li, Y., Liu, Z., Wang, X., Shang, X., Cui, Y., Zhang, Z. G., and Chopp, M. MiR-133b promotes neural plasticity and functional recovery after treatment of stroke with multipotent mesenchymal stromal cells in rats via transfer of exosome-enriched extracellular particles. *Stem Cells* 31, 2737-2746 (2013).
41. Guarnieri, D. J., and DiLeone, R. J. MicroRNAs: a new class of gene regulators. *Ann Med* 40, 197-208 (2008).
42. Lee, R. C., Feinbaum, R. L., and Ambros, V. The C. elegans heterochronic gene lin-4 encodes small RNAs with antisense complementarity to lin-14. *Cell* 75, 843-854 (1993).
43. Reinhart, B. J., Slack, F. J., Basson, M., Pasquinelli, A. E., Bettinger, J. C., Rougvie, A. E., Horvitz, H. R., and Ruvkun, G. The 21-nucleotide let-7 RNA regulates developmental timing in Caenorhabditis elegans. *Nature* 403, 901-906 (2000).
44. Janssen, H. L., Reesink, H. W., Lawitz, E. J., Zeuzem, S., Rodriguez-Torres, M., Patel, K., van der Meer, A. J., Patick, A. K., Chen, A., Zhou, Y., Persson, R., King, B. D., Kauppinen, S., Levin, A. A., and Hodges, M. R. Treatment of HCV infection by targeting microRNA. *N Engl J Med* 368, 1685-1694 (2013).
45. Mirna Therapeutics Inc. http://www.mirnarx.com/pipeline/mirna-MRX34.html. (2014).
46. Garzon, R., Marcucci, G., and Croce, C. M. Targeting microRNAs in cancer: rationale, strategies and challenges. *Nat Rev Drug Discov* 9, 775-789 (2010).
47. Rupaimoole, R., and Slack, F. J. MicroRNA therapeutics: towards a new era for the management of cancer and other diseases. *Nat Rev Drug Discov* 16, 203-222 (2017).
48. Prins, M., Greco, T., Alexander, D., and Giza, C. C. The pathophysiology of traumatic brain injury at a glance. *Dis Model Mech* 6, 1307-1315 (2013).
49. Namjoshi, D. R., Good, C., Cheng, W. H., Panenka, W., Richards, D., Cripton, P. A., and Wellington, C. L. Towards clinical management of traumatic brain injury: a review of models and mechanisms from a biomechanical perspective. *Dis Model Mech* 6, 1325-1338 (2013).
50. Gaetz, M. The neurophysiology of brain injury. *Clin Neurophysiol* 115, 4-18 (2004).
51. Perel, P., Roberts, I., Bouamra, O., Woodford, M., Mooney, J., and Lecky, F. Intracranial bleeding in patients with traumatic brain injury: a prognostic study. *BMC Emerg Med* 9, 15 (2009).
52. Keep, R. F., Hua, Y., and Xi, G. Intracerebral haemorrhage: mechanisms of injury and therapeutic targets. *Lancet Neurol* 11, 720-731 (2012).

53. NINDS. Traumatic Brain Injury: Hope Through Research. http://www.ninds.nih.gov/disorders/tbi/detail tbi.htm (2013).
54. Powers, W. J. Intracerebral hemorrhage and head trauma: common effects and common mechanisms of injury. *Stroke* 41, S107-110 (2010).
55. Agarwal, V., Bell, G. W., Nam, J. W., and Bartel, D. P. Predicting effective microRNA target sites in mammalian mRNAs. *Elife* 4(2015).
56. Kuhn, D. E., Martin, M. M., Feldman, D. S., Terry, A. V., Jr., Nuovo, G. J., and Elton, T. S. Experimental validation of miRNA targets. *Methods* 44, 47-54 (2008).
57. Staton, A. A., and Giraldez, A. J. Use of target protector morpholinos to analyze the physiological roles of specific miRNA-mRNA pairs in vivo. *Nat Protoc* 6, 2035-2049 (2011).
58. Wylie, A. D., Fleming, J. A., Whitener, A. E., and Lekven, A. C. Post-transcriptional regulation of wnt8a is essential to zebrafish axis development. *Dev Biol* 386, 53-63 (2014).
59. Liu, C., Lou, C. H., Shah, V., Ritter, R., Talley, J., Soibam, B., Benham, A., Zhu, H., Perez, E., Shieh, Y. E., Gunaratne, P. H., and Sater, A. K. Identification of microRNAs and microRNA targets in *Xenopus* gastrulae: The role of miR-26 in the regulation of Smad1. *Dev Biol* 409, 26-38 (2016).
60. Balakathiresan, N., Bhomia, M., Chandran, R., Chavko, M., McCarron, R. M., and Maheshwari, R. K. MicroRNA let-7i is a promising serum biomarker for blast-induced traumatic brain injury. *J Neurotrauma* 29, 1379-1387 (2012).
61. Redell, J. B., Moore, A. N., Ward, N. H., 3rd, Hergenroeder, G. W., and Dash, P. K. Human traumatic brain injury alters plasma microRNA levels. *J Neurotrauma* 27, 2147-2156 (2010).
62. Chang, H. I., and Yeh, M. K. Clinical development of liposome-based drugs: formulation, characterization, and therapeutic efficacy. *Int J Nanomedicine* 7, 49-60 (2012).
63. Dixon, C. E., Lyeth, B. G., Povlishock, J. T., Findling, R. L., Hamm, R. J., Marmarou, A., Young, H. F., and Hayes, R. L. A fluid percussion model of experimental brain injury in the rat. *J Neurosurg* 67, 110-119 (1987).
64. McIntosh, T. K., Vink, R., Noble, L., Yamakami, I., Fernyak, S., Soares, H., and Faden, A. L. Traumatic brain injury in the rat: characterization of a lateral fluid-percussion model. *Neuroscience* 28, 233-244 (1989).
65. Zhang, Y., Yan, L. X., Wu, Q. N., Du, Z. M., Chen, J., Liao, D. Z., Huang, M. Y., Hou, J. H., Wu, Q. L., Zeng, M. S., Huang, W. L., Zeng, Y. X., and Shao, J. Y. miR-125b is methylated and functions as a tumor suppressor by regulating the ETS1 proto-oncogene in human invasive breast cancer. *Cancer Res* 71, 3552-3562 (2011).
66. Feliciano, A., Castellvi, J., Artero-Castro, A., Leal, J. A., Romagosa, C., Hernandez-Losa, J., Peg, V., Fabra, A., Vidal, F., Kondoh, H., Ramon, Y. C. S., and Lleonart, M. E. miR-125b acts as a tumor suppressor in breast tumorigenesis via its novel direct targets ENPEP, CK2-alpha, CCNJ, and MEGF9. *PLoS One* 8, e76247 (2013).
67. Tsai, W. C., Hsu, P. W., Lai, T. C., Chau, G. Y., Lin, C. W., Chen, C. M., Lin, C. D., Liao, Y. L., Wang, J. L., Chau, Y. P., Hsu, M. T., Hsiao, M., Huang, H. D., and Tsou, A. P. MicroRNA-122, a tumor suppressor microRNA that regulates intrahepatic metastasis of hepatocellular carcinoma. *Hepatology* 49, 1571-1582 (2009).
68. Simerzin, A., Zorde-Khvalevsky, E., Rivkin, M., Adar, R., Zucman-Rossi, J., Couchy, G., Roskams, T., Govaere, O., Oren, M., Giladi, H., and Galun, E. The liver-specific microRNA-122*, the complementary strand of microRNA-122, acts as a tumor suppressor by modulating the p53/mouse double minute 2 homolog circuitry. *Hepatology* 64, 1623-1636 (2016).
69. Christopher, A. F., Kaur, R. P., Kaur, G., Kaur, A., Gupta, V., and Bansal, P. MicroRNA therapeutics: Discovering novel targets and developing specific therapy. *Perspect Clin Res* 7, 68-74 (2016).
70. Liu, D. Z., Jickling, G. C., Stamova, B., Zhan, X., Ander, B. P., and Sharp, F. R. In *Vascular Mechanisms in CNS Trauma* (Lo, E. H., Lok, J., Ning, M. M., and Whalen, M. J., eds) Vol. 5 pp. 445-457, Springer Press(2014)
71. Arroyo, J. D., Chevillet, J. R., Kroh, E. M., Ruf, I. K., Pritchard, C. C., Gibson, D. F., Mitchell, P. S., Bennett, C. F., Pogosova-Agadjanyan, E. L., Stirewalt, D. L., Tait, J. F., and Tewari, M. Argonaute2 complexes carry a population of circulating microRNAs independent of vesicles in human plasma. *Proc Natl Acad Sci USA* 108, 5003-5008 (2011).
72. Mitchell, P. S., Parkin, R. K., Kroh, E. M., Fritz, B. R., Wyman, S. K., Pogosova-Agadjanyan, E. L., Peterson, A., Noteboom, J., O'Briant, K. C., Allen, A., Lin, D. W., Urban, N., Drescher, C. W., Knudsen, B. S., Stirewalt, D. L., Gentleman, R., Vessella, R. L., Nelson, P. S., Martin, D. B., and Tewari, M. Circulating microRNAs as stable blood-based markers for cancer detection. *Proc Natl Acad Sci USA* 105, 10513-10518 (2008).
73. Wang, Z., Lu, Y., and Han, J. Peripheral blood microRNAs: A novel tool for diagnosing disease? *Intractable Rare Dis Res* 1, 98-102 (2012).
74. Hannon, G. J. RNA interference. *Nature* 418, 244-251 (2002).
75. Reynolds, A., Leake, D., Boese, Q., Scaringe, S., Marshall, W. S., and Khvorova, A. Rational siRNA design for RNA interference. *Nat Biotechnol* 22, 326-330 (2004).
76. Tokatlian, T., and Segura, T. siRNA applications in nanomedicine. *Wiley Interdiscip Rev Nanomed Nanobiotechnol* 2, 305-315 (2010).
77. Whitehead, K. A., Langer, R., and Anderson, D. G. Knocking down barriers: advances in siRNA delivery. *Nat Rev Drug Discov* 8, 129-138 (2009).
78. Gronberg, N. V., Johansen, F. F., Kristiansen, U., and Hasseldam, H. Leukocyte infiltration in experimental stroke. *J Neuroinflammation* 10, 115 (2013).
79. Macrez, R., Ali, C., Toutirais, O., Le Mauff, B., Defer, G., Dirnagl, U., and Vivien, D. Stroke and the immune system: from pathophysiology to new therapeutic strategies. *Lancet Neurol* 10, 471-480 (2011).
80. Eltzschig, H. K., and Eckle, T. Ischemia and reperfusion—from mechanism to translation. *Nat Med* 17, 1391-1401 (2011).
81. Iadecola, C., and Anrather, J. The immunology of stroke: from mechanisms to translation. *Nat Med* 17, 796-808 (2011).
82. Hallenbeck, J. M., Hansson, G. K., and Becker, K. J. Immunology of ischemic vascular disease: plaque to attack. *Trends Immunol* 26, 550-556 (2005).
83. Swanson, R. A., Morton, M. T., Tsao-Wu, G., Savalos, R. A., Davidson, C., and Sharp, F. R. A semiautomated method for measuring brain infarct volume [see comments]. *J Cereb Blood Flow Metab* 10, 290-293 (1990).
84. Wang, T., Van, K. C., Gavin, B. J., Grayson, J. K., Lu, Y. C., Lyeth, B. G., and Pichakron, K. O. Effect of fish oil supplementation in a rat model of multiple mild traumatic brain injuries. *Restor Neurol Neurosci* 31, 647-659 (2013).

85. Lee, L. L., Galo, E., Lyeth, B. G., Muizelaar, J. P., and Berman, R. F. Neuroprotection in the rat lateral fluid percussion model of traumatic brain injury by SNX-185, an N-type voltage-gated calcium channel blocker. *Exp Neurol* 190, 70-78 (2004).
86. Liu, D. Z., Ander, B. P., Tian, Y., Stamova, B., Jickling, G. C., Davis, R. R., and Sharp, F. R. Integrated analysis of mRNA and microRNA expression in mature neurons, neural progenitor cells and neuroblastoma cells. *Gene* 495, 120-127 (2012).
87. Vorhees, C. V. & Williams, M. T. Morris water maze: procedures for assessing spatial and related forms of learning and memory. *Nat Protoc* 1, 848-858, (2006).

What is claimed is:

1. A method for reducing the severity of a traumatic brain injury (TBI) in a subject, the method comprising administering to the subject a therapeutically effective amount of a microRNA (miR) or a mimic thereof, wherein the miR is miR-125b 5p.

2. The method of claim 1, wherein the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2.

3. The method of claim 2, wherein the miR or the mimic thereof decreases the expression level of at least one gene selected from the group consisting of Mknk2, Alpk3, and Neu1.

4. The method of claim 2, wherein the expression level is decreased at least 1.5 fold relative to the expression level of the gene prior to the administration of the miR or the mimic thereof.

5. The method of claim 1, wherein the miR-125b-5p comprises a nucleotide sequence having at least 90% sequence identity to UCCCUGAGACCCUAACUUGUGA (SEQ ID NO:1).

6. A method for reducing neuronal death after a traumatic brain injury (TBI) in a subject, the method comprising administering to the subject a therapeutically effective amount of a microRNA (miR) or a mimic thereof, wherein the miR is miR-125b 5p.

7. The method of claim 6, wherein the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2.

8. The method of claim 7, wherein the miR or the mimic thereof decreases the expression level of at least one gene selected from the group consisting of Mknk2, Alpk3, and Neu1.

9. The method of claim 7, wherein the expression level is decreased at least 1.5 fold relative to the expression level of the gene prior to the administration of the miR or the mimic thereof.

10. The method of claim 6, wherein the miR-125b-5p comprises a nucleotide sequence having at least 90% sequence identity to UCCCUGAGACCCUAACUUGUGA (SEQ ID NO:1).

11. A method for reducing leukocyte infiltration after a traumatic brain injury (TBI) in a subject, the method comprising administering to the subject a therapeutically effective amount of a microRNA (miR) or a mimic thereof, wherein the miR is miR-125b 5p.

12. The method of claim 11, wherein the miR or the mimic thereof decreases the expression level of at least one gene selected from the group consisting of Mknk2, Alpk3, Neu1, Bap1, Map3k10, Tjap1, Mapre2, Asb13, Zdhhc9, Rnf217, Fam53c, Zbtb38, Ino80d, Sufu, Dusp7, Coro2b, Wipf2, Bmpr2, Pip4k2b, Dnajb5, and Eif5a2.

13. The method of claim 12, wherein the miR or the mimic thereof decreases the expression level of at least one gene selected from the group consisting of Mknk2, Alpk3, and Neu1.

14. The method of claim 12, wherein the expression level is decreased at least 1.5 fold relative to the expression level of the gene prior to the administration of the miR or the mimic thereof.

15. The method of claim 11, wherein the miR-125b-5p comprises a nucleotide sequence having at least 90% sequence identity to UCCCUGAGACCCUAACUUGUGA (SEQ ID NO:1).

* * * * *